(12) United States Patent
Sylvia

(10) Patent No.: US 11,685,594 B2
(45) Date of Patent: *Jun. 27, 2023

(54) SPRAY CANISTER DEVICE

(71) Applicant: Bemis Manufacturing Company, Sheboygan Falls, WI (US)

(72) Inventor: Jacqueline Sylvia, Darmouth, MA (US)

(73) Assignee: BEMIS MANUFACTURING COMPANY, Sheboygan Falls, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/666,547

(22) Filed: Feb. 7, 2022

(65) Prior Publication Data

US 2022/0274771 A1    Sep. 1, 2022

Related U.S. Application Data

(63) Continuation of application No. 16/426,436, filed on May 30, 2019, now Pat. No. 11,242,192.

(51) Int. Cl.
*B65D 83/14* (2006.01)
*E03D 9/08* (2006.01)

(52) U.S. Cl.
CPC .............. *B65D 83/759* (2013.01); *E03D 9/08* (2013.01)

(58) Field of Classification Search
CPC ...... B65D 83/759; B65D 83/386; E03D 9/08; B05B 15/70
USPC ...................................... 4/222, 229
See application file for complete search history.

(56) References Cited

U.S. PATENT DOCUMENTS

| 2,875,450 | A |   | 3/1959  | Umann |
|-----------|---|---|---------|-------|
| D198,085  | S |   | 4/1964  | Rich |
| 3,810,260 | A |   | 5/1974  | Lodi |
| 3,995,326 | A |   | 12/1976 | Umann |
| 4,279,362 | A |   | 7/1981  | Pursell |
| 4,287,618 | A | * | 9/1981  | Silver ............. A47K 3/022 4/444 |

(Continued)

FOREIGN PATENT DOCUMENTS

| EM | 02502245-0001 |    | 7/2014 |
|----|---------------|----|--------|
| EP | 2138640       | A1 | 12/2009 |

(Continued)

OTHER PUBLICATIONS

U.S. Appl. No. 15/847,594, filed Dec. 19, 2019, Schwab.

(Continued)

*Primary Examiner* — Lori L Baker
(74) *Attorney, Agent, or Firm* — Michael Best & Friedrich LLP

(57) ABSTRACT

A spray canister device is provided including a canister containing a liquid product, a canister housing having an opening, a chassis element, and a tray slidably coupled to the chassis element. The canister includes an actuator cap and is positioned in the canister housing such that a nozzle of the actuator cap is positioned proximate the opening. The canister housing, and the canister positioned therein, may be engaged with the tray via at least one protruding member. Once engaged, the tray may be slidably moved along the chassis element between a retracted position and an extended position to facilitate relative movement between the canister and the canister housing to compress the actuator cap of the canister and spray the liquid product.

20 Claims, 15 Drawing Sheets

(56) References Cited

U.S. PATENT DOCUMENTS

| | | | |
|---|---|---|---|
| 4,326,308 A * | 4/1982 | Silver | E03D 9/085 4/444 |
| 4,327,560 A | 5/1982 | Leon | |
| D266,758 S | 11/1982 | Johannsen | |
| 4,422,189 A * | 12/1983 | Couvrette | E03D 9/08 4/443 |
| D279,184 S | 6/1985 | Sakamoto | |
| 4,628,548 A | 12/1986 | Kurosawa | |
| D303,966 S | 10/1989 | Fritzsche | |
| 4,903,347 A | 2/1990 | Garcia | |
| 4,987,617 A | 1/1991 | Furukawa | |
| 5,031,252 A | 7/1991 | Oyama | |
| 5,101,520 A | 4/1992 | Lockhart | |
| 5,201,080 A | 4/1993 | Tanaka | |
| 5,203,037 A | 4/1993 | Kang | |
| 5,247,711 A | 9/1993 | Kwon | |
| 5,272,774 A | 12/1993 | Ivko | |
| 5,335,855 A | 8/1994 | Borod | |
| D355,246 S | 2/1995 | Kawamura | |
| 5,409,167 A | 4/1995 | Borod | |
| D367,922 S | 3/1996 | Kobayashi | |
| 5,504,948 A | 4/1996 | Chandler | |
| 5,551,098 A | 9/1996 | Wilk | |
| 5,566,402 A | 10/1996 | Agha | |
| 5,630,234 A | 5/1997 | Childs | |
| D387,851 S | 12/1997 | Pieters | |
| 5,720,054 A | 2/1998 | Nakayama | |
| 5,765,238 A | 6/1998 | Furukawa | |
| 5,813,060 A | 9/1998 | Klopocinski | |
| 5,864,894 A | 2/1999 | Fedele | |
| 5,898,956 A | 5/1999 | Kurisaki | |
| 5,911,516 A | 6/1999 | Chang | |
| 5,953,765 A | 9/1999 | Hayashi | |
| 5,987,659 A | 11/1999 | Cannizzaro | |
| 6,003,159 A | 12/1999 | Sadegh | |
| 6,009,570 A | 1/2000 | Hargest | |
| D423,655 S | 4/2000 | Otte | |
| 6,073,275 A | 6/2000 | Klopocinski | |
| 6,105,178 A | 8/2000 | Kurisaki | |
| D432,220 S | 10/2000 | Hulsebus | |
| D435,638 S | 12/2000 | Merry | |
| 6,167,577 B1 | 1/2001 | Hammad | |
| 6,178,568 B1 | 1/2001 | Boulieris | |
| 6,192,527 B1 | 2/2001 | Paul | |
| D451,076 S | 11/2001 | Sommer | |
| D451,177 S | 11/2001 | Scholpp | |
| 6,339,852 B1 | 1/2002 | Huang | |
| 6,397,406 B1 | 6/2002 | Moshkovich | |
| 6,430,366 B1 | 8/2002 | Mizutani | |
| 6,449,780 B1 | 9/2002 | Merry | |
| 6,481,590 B1 | 11/2002 | Simkins | |
| D471,966 S | 3/2003 | Takahashi | |
| D481,016 S | 10/2003 | Hillis | |
| D485,337 S | 1/2004 | Tani | |
| 6,688,500 B1 | 2/2004 | Cheng | |
| 6,754,912 B1 | 6/2004 | Hayashi | |
| D500,130 S | 12/2004 | Jung | |
| D508,733 S | 8/2005 | Peng | |
| D512,425 S | 12/2005 | Nakagawa | |
| 6,973,679 B1 | 12/2005 | Schad | |
| 7,096,518 B2 | 8/2006 | Takenaga | |
| D528,991 S | 9/2006 | Katsuyama | |
| 7,120,946 B1 | 10/2006 | Lazar | |
| 7,127,750 B2 * | 10/2006 | Lim | A47K 13/00 4/420.4 |
| D533,788 S | 12/2006 | Kleiman | |
| 7,155,755 B2 | 1/2007 | Olivier | |
| D538,907 S | 3/2007 | Kaule | |
| 7,191,473 B2 | 3/2007 | Matsumoto | |
| D541,225 S | 4/2007 | Katsuyama | |
| 7,216,374 B2 | 5/2007 | Hassan | |
| 7,284,285 B2 | 10/2007 | Scalzi | |
| 7,287,286 B2 | 10/2007 | Lee | |
| D554,613 S | 11/2007 | Nakatani | |
| D558,181 S | 12/2007 | Takada | |
| D564,976 S | 3/2008 | Jackson | |
| D565,554 S | 4/2008 | Fan | |
| D578,515 S | 10/2008 | Ikeda | |
| D579,342 S | 10/2008 | Priestman | |
| D583,030 S | 12/2008 | Kobayashi | |
| D594,537 S | 6/2009 | Driedger | |
| D594,945 S | 6/2009 | Nakasaki | |
| 7,543,339 B1 | 6/2009 | Harris | |
| D608,426 S | 1/2010 | Watanabe | |
| D616,445 S | 5/2010 | Wong | |
| D634,735 S | 3/2011 | Maier | |
| D639,399 S | 6/2011 | Takeuchi | |
| D639,400 S | 6/2011 | Kang | |
| 7,954,181 B2 | 6/2011 | Lim | |
| 8,060,953 B1 | 11/2011 | Dorra | |
| 8,065,755 B2 | 11/2011 | Chen | |
| D654,808 S | 2/2012 | Gidlow | |
| 8,161,580 B2 | 4/2012 | Hashidume | |
| 8,261,377 B2 | 9/2012 | Oh | |
| D668,642 S | 10/2012 | Feldman | |
| 8,291,527 B2 | 10/2012 | Pan | |
| D670,659 S | 11/2012 | Yoshioka | |
| D671,935 S | 12/2012 | Mao | |
| 8,365,317 B1 | 2/2013 | Dorra | |
| 8,425,475 B2 | 4/2013 | Sodo | |
| D682,246 S | 5/2013 | Boqueho | |
| D688,359 S | 8/2013 | Ogata | |
| D692,417 S | 10/2013 | Tu | |
| D692,541 S | 10/2013 | Hosoi et al. | |
| D698,754 S | 2/2014 | Vignau-Lous | |
| D703,797 S | 4/2014 | Shinozaki | |
| D704,316 S | 5/2014 | Yoshioka | |
| D704,317 S | 5/2014 | Ando | |
| D706,402 S | 6/2014 | Yeung | |
| D708,954 S | 7/2014 | Barnes | |
| 8,776,278 B1 | 7/2014 | Dorra | |
| D713,815 S | 9/2014 | Ookawa | |
| D715,774 S | 10/2014 | Lee et al. | |
| D716,768 S | 11/2014 | Kim | |
| D717,930 S | 11/2014 | Kergoet | |
| 8,904,575 B1 | 12/2014 | Lindheimer | |
| D724,058 S | 3/2015 | Chandel | |
| D724,059 S | 3/2015 | Kim | |
| D750,765 S | 3/2016 | Giametta | |
| 9,273,454 B2 | 3/2016 | Slawinski | |
| 9,279,241 B2 | 3/2016 | Morioka | |
| D753,095 S | 4/2016 | Moran | |
| 9,464,425 B2 | 10/2016 | Bailey | |
| D781,808 S | 3/2017 | Pista | |
| D792,867 S | 7/2017 | Murphy | |
| D805,615 S | 12/2017 | Peng | |
| 9,889,982 B2 | 2/2018 | Falcon | |
| 2003/0140407 A1 | 7/2003 | Matsumoto | |
| 2004/0050959 A1 | 3/2004 | Mazooji | |
| 2004/0055080 A1 | 3/2004 | Marshall | |
| 2005/0000006 A1 | 1/2005 | Takenaga | |
| 2005/0010997 A1 | 1/2005 | Olivier | |
| 2006/0000012 A1 | 1/2006 | Schad | |
| 2006/0047055 A1 | 3/2006 | Agostini | |
| 2006/0207002 A1 | 9/2006 | Bradshaw | |
| 2006/0265801 A1 | 11/2006 | Riccobon | |
| 2007/0241929 A1 | 10/2007 | Marchetto | |
| 2008/0055394 A1 | 3/2008 | Shiue | |
| 2008/0201837 A1 | 8/2008 | Oh | |
| 2008/0251551 A1 | 10/2008 | Huber | |
| 2009/0313752 A1 * | 12/2009 | Kunimoto | E03D 9/08 4/662 |
| 2010/0012685 A1 | 1/2010 | Ramsey | |
| 2010/0152475 A1 | 6/2010 | Raichle | |
| 2010/0176224 A1 | 7/2010 | Hasselschwert | |
| 2011/0113540 A1 | 5/2011 | Plate | |
| 2011/0132929 A1 | 6/2011 | Bennett | |
| 2011/0191950 A1 | 8/2011 | Liu | |
| 2011/0203044 A1 | 8/2011 | Lim | |
| 2012/0005817 A1 | 1/2012 | Jeong | |
| 2012/0011647 A1 | 1/2012 | Mochita | |
| 2012/0150148 A1 | 6/2012 | Shi | |
| 2012/0180785 A1 | 7/2012 | Trill | |
| 2012/0218106 A1 | 8/2012 | Zaima | |

(56) References Cited

U.S. PATENT DOCUMENTS

| | | |
|---|---|---|
| 2012/0266483 A1 | 10/2012 | Palermo |
| 2013/0133131 A1 | 5/2013 | Peng |
| 2013/0267890 A1 | 10/2013 | Li |
| 2014/0042195 A1 | 2/2014 | Geis |
| 2014/0047626 A1 | 2/2014 | Dorra |
| 2014/0068862 A1 | 3/2014 | Al-Jafar |
| 2014/0107409 A1 | 4/2014 | Bailey |
| 2014/0373263 A1 | 12/2014 | Plate |
| 2015/0000025 A1 | 1/2015 | Clements |
| 2015/0059076 A1 | 3/2015 | Tiagai |
| 2015/0203279 A1 | 7/2015 | Falcon |
| 2015/0225167 A1 | 8/2015 | Andersen |
| 2015/0337525 A1 | 11/2015 | Bailey |
| 2015/0354190 A1 | 12/2015 | Willers |
| 2016/0010319 A1 | 1/2016 | Willers |
| 2016/0316978 A1 | 11/2016 | Peng |
| 2017/0021116 A1 | 1/2017 | Rahmel |
| 2017/0101838 A1 | 4/2017 | Razvi |
| 2017/0142306 A1 | 5/2017 | Peng |
| 2017/0265624 A1 | 9/2017 | Wilson |
| 2017/0319794 A1 | 11/2017 | Schwab |
| 2017/0321406 A1 | 11/2017 | Schwab |
| 2017/0321407 A1 | 11/2017 | Schwab |
| 2017/0321408 A1 | 11/2017 | Schwab |
| 2018/0015238 A1 | 1/2018 | Schwab |
| 2018/0028797 A1 | 2/2018 | Schwab |
| 2018/0036473 A1 | 2/2018 | Schwab |
| 2018/0044903 A1* | 2/2018 | Schwab .................... E03D 9/08 |

FOREIGN PATENT DOCUMENTS

| | | |
|---|---|---|
| IN | 2689190001 | 10/2015 |
| JP | H0893034 A | 4/1996 |
| JP | H0988165 A | 3/1997 |
| JP | H1163666 A | 3/1999 |
| JP | 2001279778 A | 10/2001 |
| JP | 2010084344 A | 4/2010 |
| KR | 20030064724 A | 8/2003 |
| KR | 100786217 B1 | 12/2007 |
| KR | 1020090127708 A | 12/2009 |
| KR | 1020120083971 A | 7/2012 |
| KR | 1020120006514 U | 9/2012 |
| KR | 101320587 B1 | 10/2013 |
| WO | 2008024005 A2 | 2/2008 |
| WO | 2013020240 A1 | 2/2013 |
| WO | 2012044086 A2 | 4/2017 |

OTHER PUBLICATIONS

Final Office Action for U.S. Appl. No. 15/588,640 dated Dec. 3, 2018.

International Search Report and Written Opinion for Application No. PCT/US2020/041966 dated Dec. 10, 2020.

International Search Report and Written Opinion for Application No. PCT/US2020/070018 dated Aug. 28, 2020.

Kohler, "Self-Cleaning Wand", <https:///www.youtube.com/watch?v=z629hpdnWj8> published Oct. 12, 2016.

PCT Notification of Transmittal of The International Search Report and The Written Opinion of The International Searching Authority, or Declaration, PCT/U2017/031482, filed on May 6, 2017 by Whole Bath, LLC.

PCT Notification of Transmittal of the International Search Report and The Written Opinion of The International Searching Authority, or Declaration, PCT/US2017/031483, filed on May 6, 2017 by Whole Bath, LLC.

PCT Notification of Transmittal of The International Search Report and The Written Opinion of The International Searching Authority, or Declaration; PCT/US2017/031484, filed on May 6, 2017 by Whole Bath, LLC.

PCT Notification of Transmittal of the International Search Report and The Written Opinion of The International Searching Authority, or Declaration; PCT/US2017/031485, filed on May 6, 2017 by Whole Bath, LLC.

PCT Notification of Transmittal of The International Search Report and The Written Opinion of The International Searching Authority, PCT/US2016/45932, dated Oct. 24, 2016.

PCT Notification of Transmittal of The International Search Report and The Written Opinion of The International Searching Authority, PCT/US2017/042288, dated Sep. 28, 2017.

PCT Notification of Transmittal of The International Search Report and The Written Opinion of The International Searching Authority, PCT/US2017/42253, dated Nov. 21, 2017.

PCT Notification of Transmittal of The International Searchc Report and The Written Opinion of the International Searching Authority, PCT/US2017031484, dated Aug. 14, 2017.

Schwabcare website 2017, <http://schwabcare.com/>, site visited Jan. 21, 2018.

* cited by examiner

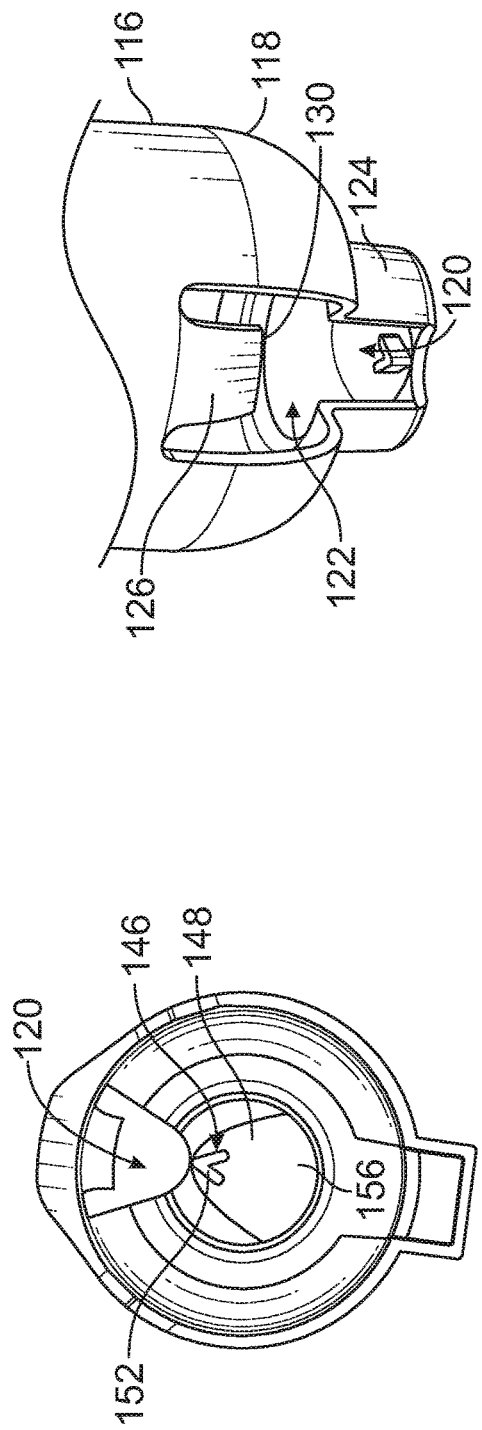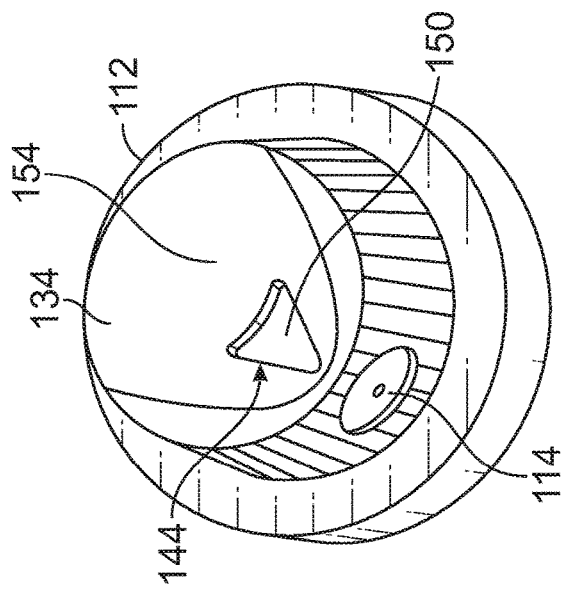
FIG. 6A
FIG. 6B
FIG. 7

SPRAY CANISTER DEVICE

FIELD

This disclosure relates to a spray canister device, and more specifically, a spray canister device for use in a toilet seat assembly.

BACKGROUND

Toilet seat assemblies, such as those including a bidet, are known for washing and cleaning the perineal region of a user. Such assemblies are also of interest in the medical field for individuals who may not be able to effectively care for themselves and otherwise wash or clean themselves without assistance. For many of these individuals, excess moisture in the perineal region becomes a continuous problem. For example, excess moisture can cause redness, peeling, irritation, yeast infections, among other issues. Although known toilet seat assemblies are configured for washing and drying the perineal region of a user, such skin problems may still develop. To address these concerns, various medicaments or sprays may be applied to the perineal region of an individual to protect the skin from excessive moisture due to incontinence, wound drainage, or perspiration.

Such medicaments may be incorporated into a toilet seat assembly such that they may be applied after a washing and drying operation to further prevent skin breakdown or infection due to excessive moisture build up. To dispense the medicaments, the toilet seat assembly may include an atomizing spray assembly configured to spray the medicament onto the perineal region. However, for individuals that may not be as dexterous due to old age or other associated conditions such as arthritis, replacement of medicament canisters can become difficult. Currently available options present certain challenges for less dexterous individuals as replacement of the canister requires precise alignment within the toilet seat assembly.

It would be beneficial to have a spray canister device for a toilet seat assembly for dispensing medicaments that can be reliably installed and removed with an improved alignment structure to ensure the spray canister device is properly aligned without requiring the user to manually perform the alignment during installation.

BRIEF DESCRIPTION OF THE DRAWINGS

FIG. 6A is a top plan view of the canister housing showing an interior thereof, and a V-shaped protrusion on an interior surface of the cap-shaped portion of the canister housing;

FIG. 6B is a perspective view of a portion of the canister housing showing the opening, the protruding finger portion, and the V-shaped protrusion;

FIG. 7 is a perspective view of the actuator cap of the canister showing the nozzle and a recessed notch corresponding with the V-shaped protrusion in the interior of the cap-shaped portion of the canister housing;

DETAILED DESCRIPTION

Figure 1:
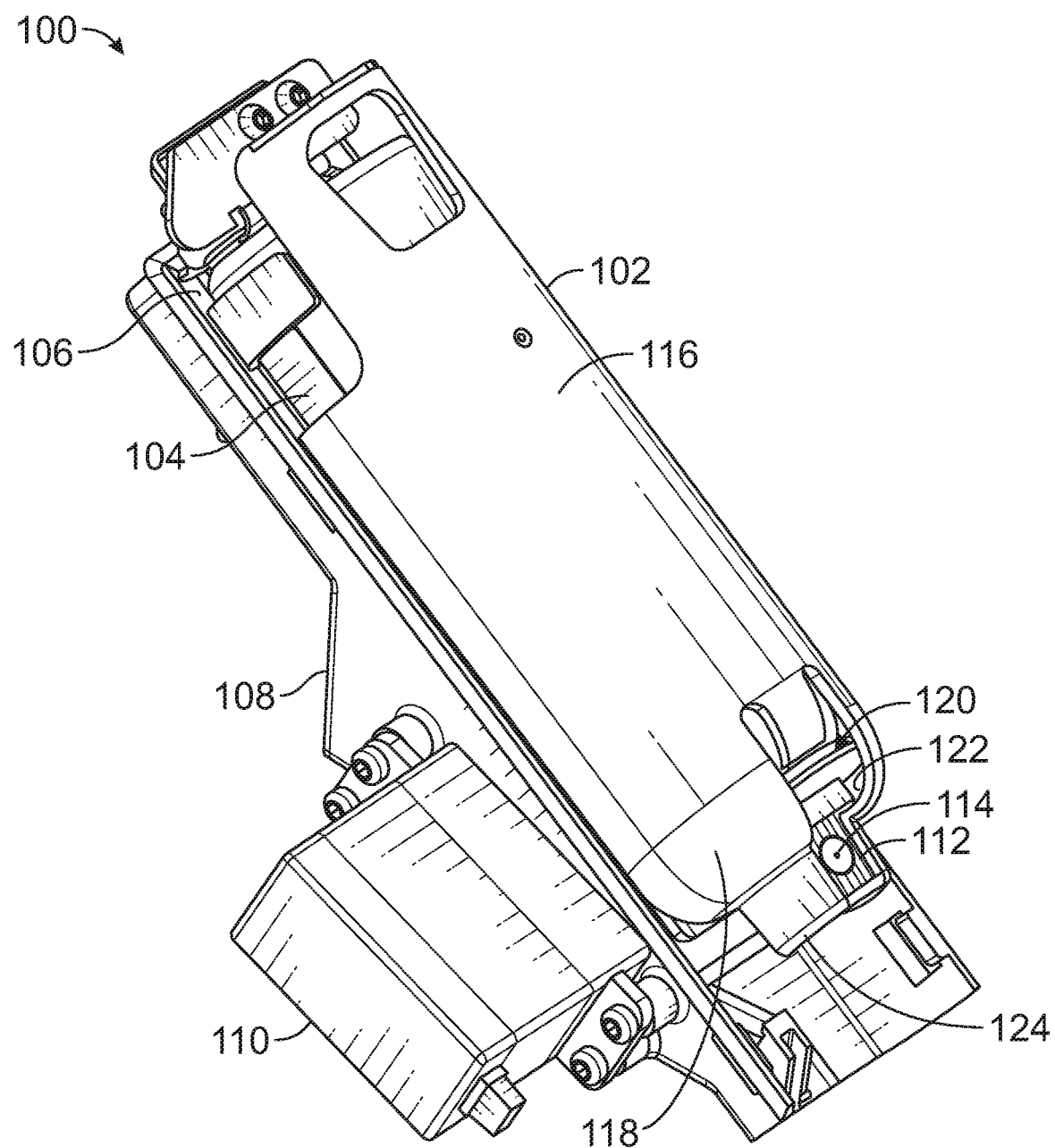
FIG. 1 is a perspective view of a spray canister device including a canister housing, a canister, and a tray slidably coupled to a chassis element and connected to a motor to cause slidable movement of the tray.

In accordance with the present disclosure, a spray canister device is provided including a canister containing a liquid product, a canister housing having an opening, a chassis element, and a tray slidably coupled to the chassis element. The canister includes an actuator cap and, during use, is positioned on the canister housing such that a nozzle of the actuator cap is positioned proximate the opening. The canister housing, and the canister positioned therein, may be engaged with the tray via at least one protruding member. Once engaged, the tray may be slidably moved along the chassis element between a retracted position and an extended position to facilitate relative movement between the canister and the canister housing to compress the actuator cap of the canister and spray the liquid product. By one approach, the retracted position is used for storage of the canister and the extended position is used for application or dispensing the liquid product from the canister.

More particularly, the spray canister device may be positioned in a toilet seat assembly such that the spray canister device may be used to apply the liquid product to the perineal region of a user. The chassis element may be positioned in the toilet seat assembly, and the tray may be slidably coupled to the chassis element as described above. A motor may be operatively coupled to the tray to slidably move the tray between a retracted position within the toilet seat assembly and an extended position extending outward from an opening in the toilet seat assembly. The canister housing and canister positioned therein may be inserted into the toilet seat assembly through an opening thereof to engage with the tray. So configured, the canister housing and canister positioned therein may be moved with the tray between the retracted position and the extended position such that the liquid product may be sprayed onto the perineal region of a user.

Additionally, the canister housing may include at least one keyed connection to facilitate alignment of the canister and canister housing within the toilet seat assembly for individuals with limited dexterity. For example, the actuator cap of the canister may include a first mating surface corresponding and configured to be engaged with a second mating surface on an interior of the canister housing to promote alignment of the nozzle with the opening such that the nozzle is not obscured or blocked by any portion of the canister housing during operation. Also, as described above, in one embodiment having an additional keyed connection, the canister housing includes at least one protruding member to engage with the tray. The tray may include a slot for receiving the protruding member of the canister housing such that the canister housing may only be engaged with the tray in a predetermined orientation, so the opening of the canister housing is positioned proximate the perineal region of a user when the tray is in the extended position. In addition, the opening of the toilet seat and the shape of the canister housing may form another keyed connection, such that the canister and canister housing may only be installed therein in a desired orientation, as described in more detail hereinafter.

So configured, these multiple keyed connections assist less dexterous users in positioning the canister in the canister housing to facilitate alignment between the nozzle and the opening of the canister housing, and subsequently inserting the canister housing and canister in the toilet seat assembly to engage with the tray.

Referring now to FIG. 1, a spray canister device 100 including a canister housing 102, a canister 104, and a tray 106 slidably coupled to a chassis element 108 is shown. A motor 110 may be secured to the chassis element 108 and operatively coupled to the tray 106 such that the tray 106 may be moved between a retracted position (see FIG. 1) and an extended position (see FIG. 13). The canister 104 contains a liquid product and includes a body 111 and an actuator cap 112 having a nozzle 114 to spray the liquid product therefrom. The canister housing 102 includes an annular sleeve portion 116, an end portion 118, and an opening 120 extending at least partially in the annular sleeve portion 116 and the end portion 118. As shown, the canister 104 is positioned in the annular sleeve portion 116 of the canister housing 102 and the actuator cap 112 is at least partially received in the end portion 118 such that the nozzle 114 is positioned proximate the opening 120. The canister housing 102 and canister 104 positioned therein may be engaged with the tray 106 as illustrated. In operation, the motor 110 may cause the tray 106 engaged with the canister housing 102 and canister 104 to slidably move the tray 106 to the extended position and move the canister housing 102 and canister 104 relative one another to compress the actuator cap 112 and spray the liquid product from the nozzle 114, as described in more detail hereinafter.

Figure 2:
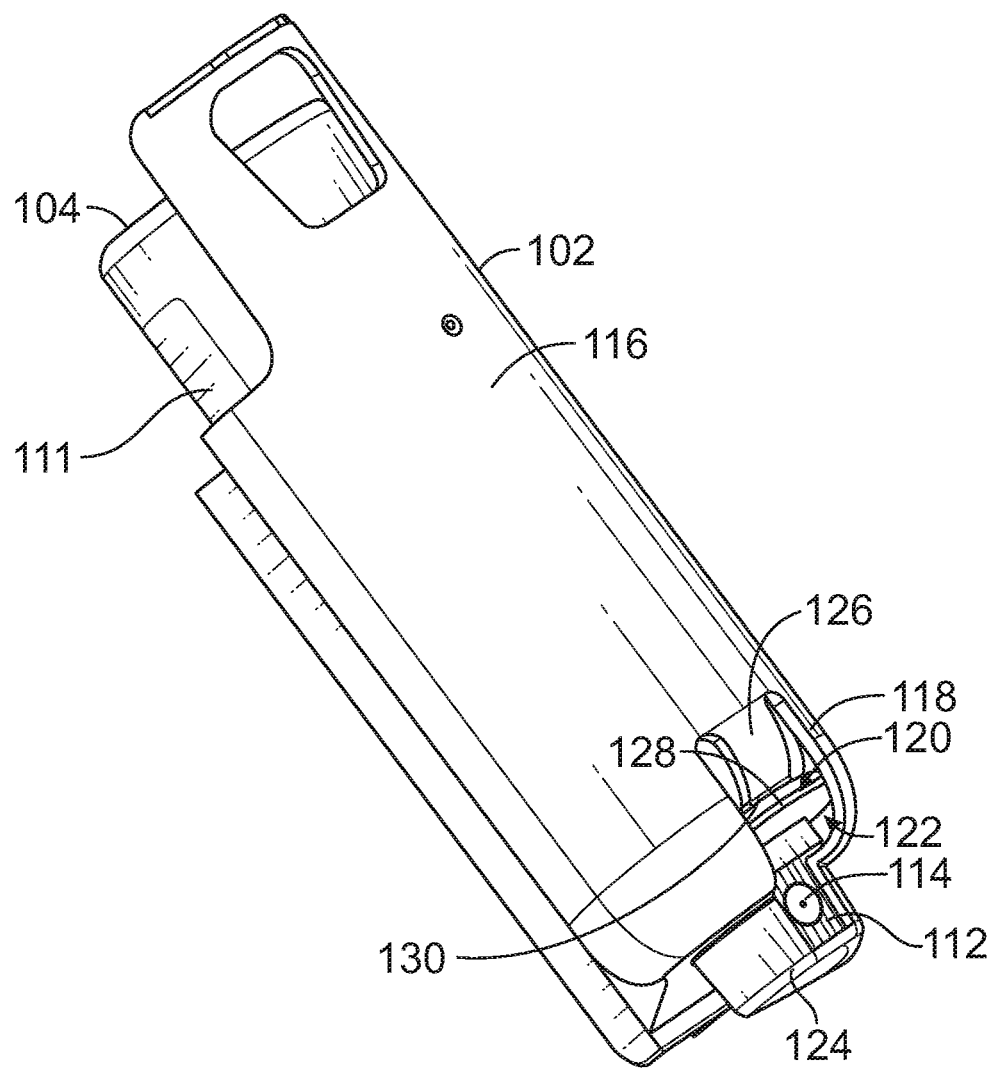
FIG. 2 is a perspective view of the canister housing and the canister of FIG. 1, with the canister positioned in a sleeve portion of the canister housing.

FIG. 2 shows a perspective view of the canister 104 positioned in the canister housing 102. As shown, the canister housing 102 is shaped to generally correspond with and receive the canister 104 at least partially therein. The canister housing 102 includes the annular sleeve portion 116 and the end portion 118 defining an interior 122 of the canister housing 102. The end portion 118 extends from the annular sleeve portion 116 and tapers radially inwards from a first, larger diameter to a second, smaller diameter and terminates in a cap-shaped portion 124 configured to receive the actuator cap 112 of the canister 104. In the illustrated embodiment, the opening 120 extends partially across both the sleeve portion 116 and the end portion 118 and permits access to the interior 122 of the canister housing 102. In other embodiments, the opening 120 may be shaped in any known manner provided the nozzle 114 of the actuator cap 112 is aligned with, and able to spray the liquid product through, the opening 120.

In one illustrative embodiment, the canister 104 is securely engaged in the canister housing 102 to inhibit accidental removal thereof which may interfere with ordinary operation of the spray canister device 100. To secure the canister 104 in the canister housing 102, a protruding finger portion 126 may be provided to engage a rim surface 128 of the canister to inhibit removal of or prevent unintentional separation of the canister 104 from the canister housing 102. As illustrated, the finger portion 126 is of a tab of a generally arcuate shape and extends radially inwards towards the interior 122 of the canister housing in the opening 120. To secure the canister 104 in the canister housing 102, the canister 104 may be axially advanced into the annular sleeve portion 116. Once the rim 128 of the canister 104 is advanced past an edge 130 of the finger portion 126, the finger portion 126 rebounds into an interference fit with the rim 128 of the canister 104 such that the edge 130 of the finger portion 126 is abutting the rim 128.

So configured, the abutment between the edge 130 of the finger portion 126 and the rim 128 of the canister 104 inhibits removal or prevents unintentional separation of the canister 104 from the canister housing 102. Additionally, the canister housing 102 may include handle portion 123 to facilitate engagement and disengagement with the tray 106, as described in more detail below.

Figure 3:
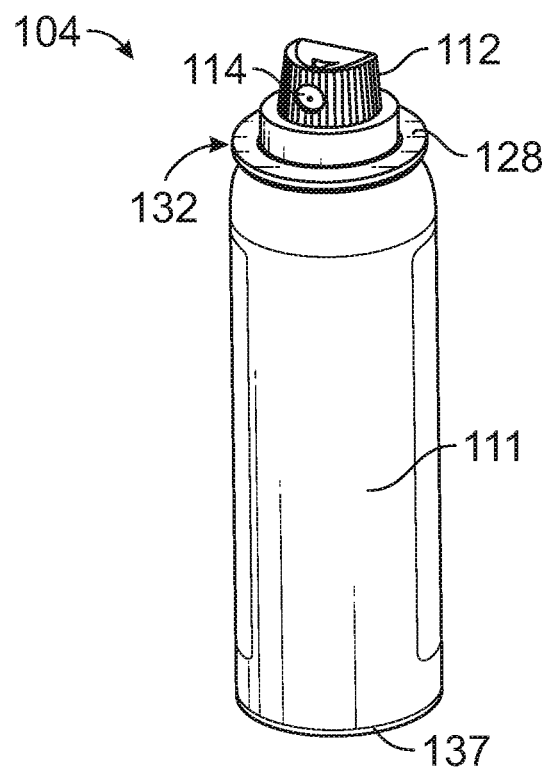
FIG. 3 is a front elevational view of the canister including an actuator cap having a spray nozzle for spraying a liquid product contained in the canister.
Figure 4:
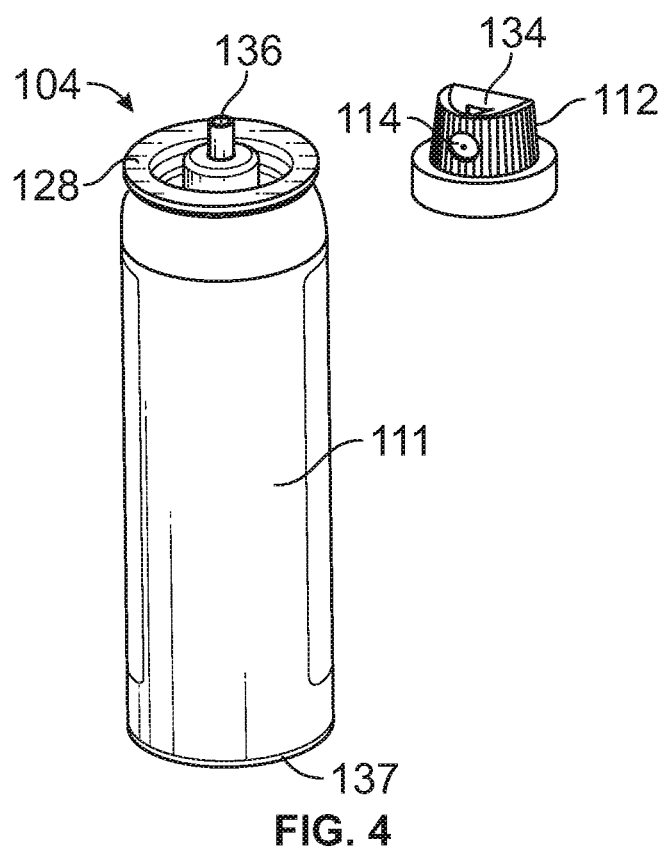
FIG. 4 is a perspective view of the canister of FIG. 3 with the actuator cap removed from the canister to show a compressible outlet thereof.

Regarding FIGS. 3 and 4, an embodiment of the canister 104 is shown isolated from the other components of the spray canister device 100. The actuator cap 112, is shown coupled to a top end 132 of the canister 104. The rim 128 of the canister 104 advances radially outwards near the top end 132 thereof. In order to spray the liquid product contained in the canister 104, a top surface 134 of the actuator cap 112 may be compressed downwards in vertical direction to compress an outlet 136 of the canister (shown in FIG. 4) to release the liquid product through the actuator cap 112 and out of the nozzle 114. As described herein, the liquid product in the canister 104 may comprise a plurality of different liquid products for application to the perineal region of a user. For example, the liquid product may comprise, but is not limited to, one or more of skin protectants, ointments, creams, zinc oxide, calamine, barrier solutions, cleaning solutions, moisturizers, skin sealants, water, medicaments, cleaning solutions, among others. In some approaches, the liquid product is a barrier solution such that the barrier solution may be applied to the perineal region of a user to protect this portion of the user's skin and inhibit excessive moisture after cleaning via, for example, a bidet. Additionally, the canister 104 includes a bottom surface 137 upon which force may be applied when the canister 104 is positioned in the canister housing 102 to compress the actuator cap 112 and spray the liquid product.

Figure 5A:
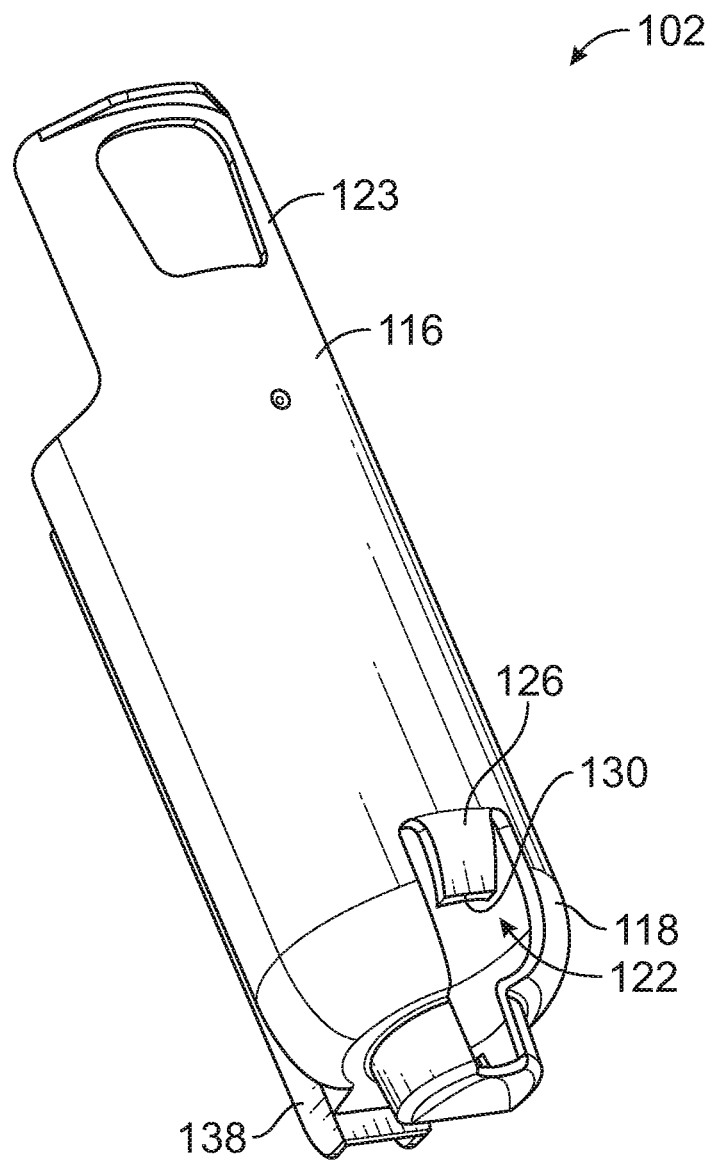
FIG. 5A is a perspective view of the canister housing having the annular sleeve portion, an end portion with a cap-shaped portion, a handle, an opening, and a protruding finger portion extending in the opening.
Figure 5B:
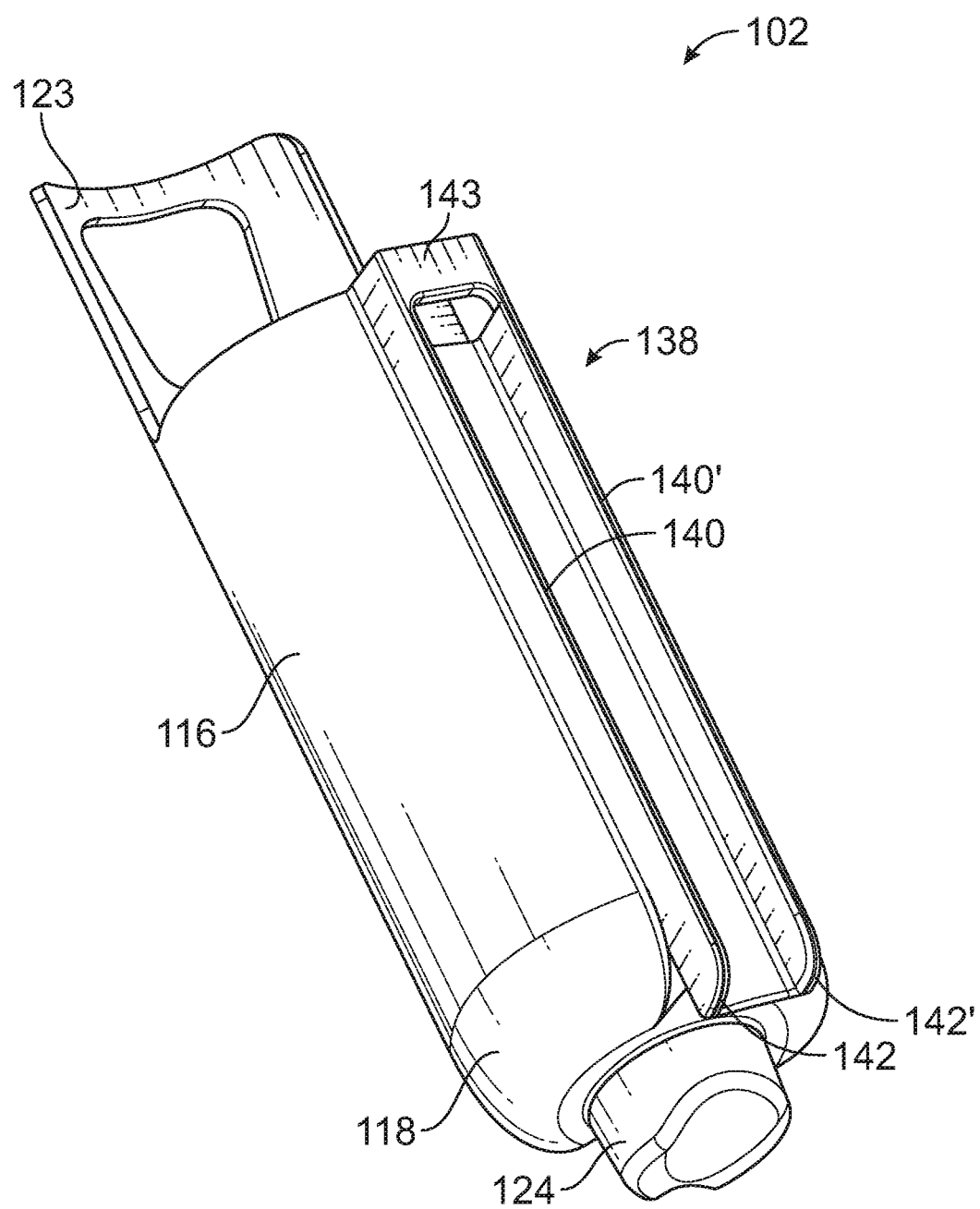
FIG. 5B is a perspective view of an opposite side of the canister housing of FIG. 5A showing two elongate rails extending along the annular sleeve portion of the canister housing and a locking structure extending therebetween.

FIGS. 5A and 5B show opposite sides of an embodiment of the canister housing 102. As described above, the canister housing 102 includes the annular sleeve portion 116 and the end portion 118 defining an interior 122 in which the canister 104 may be received. In the illustrated embodiment, the canister housing 102 comprises a unitary body or monolithic construction. In other embodiments, the canister housing 102 may comprise separate elements which may be assembled to create the canister housing 102.

FIG. 5B shows a perspective view of the opposite side of the canister housing 102 shown in FIG. 5A. As illustrated, the canister housing 102 includes a pair of protruding members 138 in the form of a first elongate rail 140 and a second elongate rail 140'. The elongate rails 140, 140' extend along the annular sleeve portion 116. A bottom edge 142, 142' of each elongate rail 140, 140' respectively may be rounded for insertion in a toilet seat assembly as described with respect to FIGS. 14A through 14F. The protruding members 138 may be engaged with corresponding slots (shown in FIG. 8) in the tray 106 to provide a keyed connection therebetween. In other embodiments, the protruding members 138 may be formed of other configurations such as a plurality of tabs or other structures configured to engage with the tray 106. In operation, the protruding members 138 facilitate alignment of the canister housing 102 when inserted into a toilet seat assembly by ensuring that the canister housing 102 maintains a desired orientation when engaged with the tray 106.

As illustrated in FIG. 5B, a locking structure 143 is included extending between the elongate rails 140, 140'. The locking structure 143 may be included to facilitate relative movement of the canister housing 102 and the canister 104 by inhibiting the canister housing 102 from advancing forwards while tray 106 continues to advance and the canister 104 is compressed by a component of the tray 106, which will be discussed in more detail hereinafter with respect to FIG. 13.

FIGS. 6A and 6B show the end portion 118 and the cap-shaped portion 124 thereof and FIG. 7 shows the top surface 134 of the actuator cap 112 that is received in the cap-shaped portion 124. Upon insertion of the canister 104 in the canister housing 102, the nozzle 114 is typically positioned proximate the opening 120 to ensure that the liquid product may be sprayed therefrom. To facilitate alignment between the nozzle 114 and the opening 120, the top surface 134 of the actuator cap 112 may include a first mating portion 144 corresponding with, and configured to engage, a second mating portion 146 on an interior surface 148 of the cap-shaped portion 124 of the canister housing 102. The engagement between the first mating portion 144 and the second mating portion 146 provides an additional keyed connection between the actuator cap 112 and the interior surface 148 of the cap-shaped portion 124. In the illustrated form of FIG. 7, the first mating portion 144 on the top surface 134 of the actuator cap 112 is in the form of a recessed, triangular notch 150. As shown in FIGS. 6A and 6B, the interior surface 148 of the cap-shaped portion 124 includes a V-shaped protrusion 152 corresponding with the recessed notch 150. So configured, the V-shaped protrusion 152 is configured to engage with the recessed notch 150 on the surface 148 when the canister 104 is inserted in the canister housing 102 to promote alignment of the nozzle 114 with the opening 120.

Additionally or alternatively, the interior surface 148 of the cap-shaped portion 124 and the top surface 134 of the actuator cap 112 may be contoured such that insertion of the canister 104 in the canister housing 102 in an orientation where the nozzle 114 is not aligned with the opening 120 will rotate the actuator cap 112 into desired alignment. For example, the top surface 134 of the actuator cap 112 may include a parabolic concave portion 154 and the interior surface 148 of the cap-shaped portion 124 may include a corresponding parabolic convex portion 156. Upon receiving the actuator cap 112 in the end portion 118 and cap-shaped portion 124 of the canister housing 102, the concave and convex portions 154, 156 may abut, causing the actuator cap 112 to rotate such that the concave and convex portions 154, 156 are matingly aligned and the nozzle 114 is positioned proximate the opening 120 when the a force is applied to one or both of the canister housing 102 or the canister 104. So configured, regardless of the direction at which the nozzle 144 is facing when the canister 104 is initially inserted in the canister housing 102, once fully inserted therein, both the contact between the parabolic concave and convex portions 154, 156 and the keyed connection between the first mating portion 144 and the second mating portion 146 promote desired alignment between the nozzle 114 and the opening 120.

Figure 8:
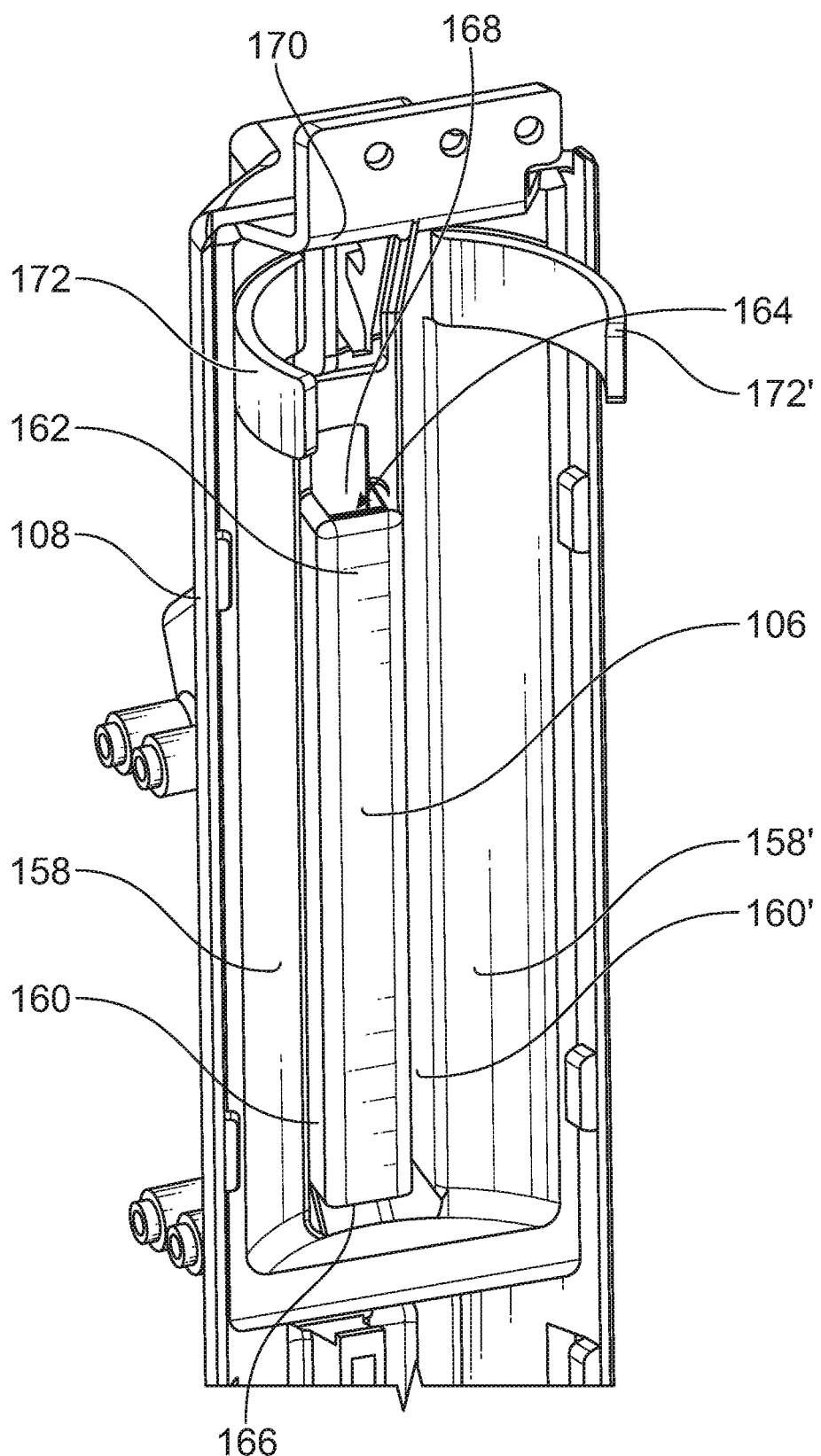
FIG. 8 is a perspective view of the tray and the chassis element of FIG. 1 showing the tray slidably coupled thereto, with a proximal side of the tray including curved sidewall portions and a pair of elongate slots for receiving the elongate rails of the canister housing, the tray further including a compression member and a pair of rib members for securing the canister.

FIG. 8 shows the tray 106 slidably coupled to the chassis element 108 with the canister housing 102 and canister 102 removed. As illustrated, the tray 106 includes curved sidewall portions 158, 158' generally shaped to correspond with and receive the annular sleeve portion 116 of the canister housing 102. The tray 106 further includes two, elongate slots 160, 160' extending parallel along a proximal side 162 thereof and defining an elongate channel 164 therebetween having a first opening 166 and a second opening 168. The elongate slots 160, 160' are configured to receive the protruding members 138 in the form of the pair of elongate rails 140, 140' of the canister housing 102 in the form of a keyed connection to promote desired alignment. So configured, the elongate rails 140, 140' rest in the slots 160, 160' akin to staple legs positioned in a stapler such that the canister housing 102 only engages with the tray 106 in the desired orientation. The tray 106 further includes a compression member 170 to abut and apply force to the bottom surface 137 of the canister 104 to compress the actuator cap 112 thereof to spray the liquid product therefrom, as discussed in more detail hereinafter.

As illustrated, the tray 106 may additionally include at least two rib members 172, 172' for securing the canister 104 and canister housing 102 to the tray 106. In one illustrative embodiment, the rib members 172, 172' have a generally arcuate configuration and are configured to wrap partially around a portion of the canister 104 to secure the canister 104 and canister housing 102 to the tray 106. The rib members 172, 172' may be of a flexible or semi-flexible plastic such that they may be snap fit around all or a portion of the outer surface of the canister 104. Once the canister 104 is positioned in the canister housing 102, the elongate rails 140, 140' may be advanced into the slots 160, 160' of the tray 106 and the canister 104 may be snap-fit between the ribs 172, 172' to releasably secure the canister 104 and canister housing 102 to the tray 106.

Figure 9:
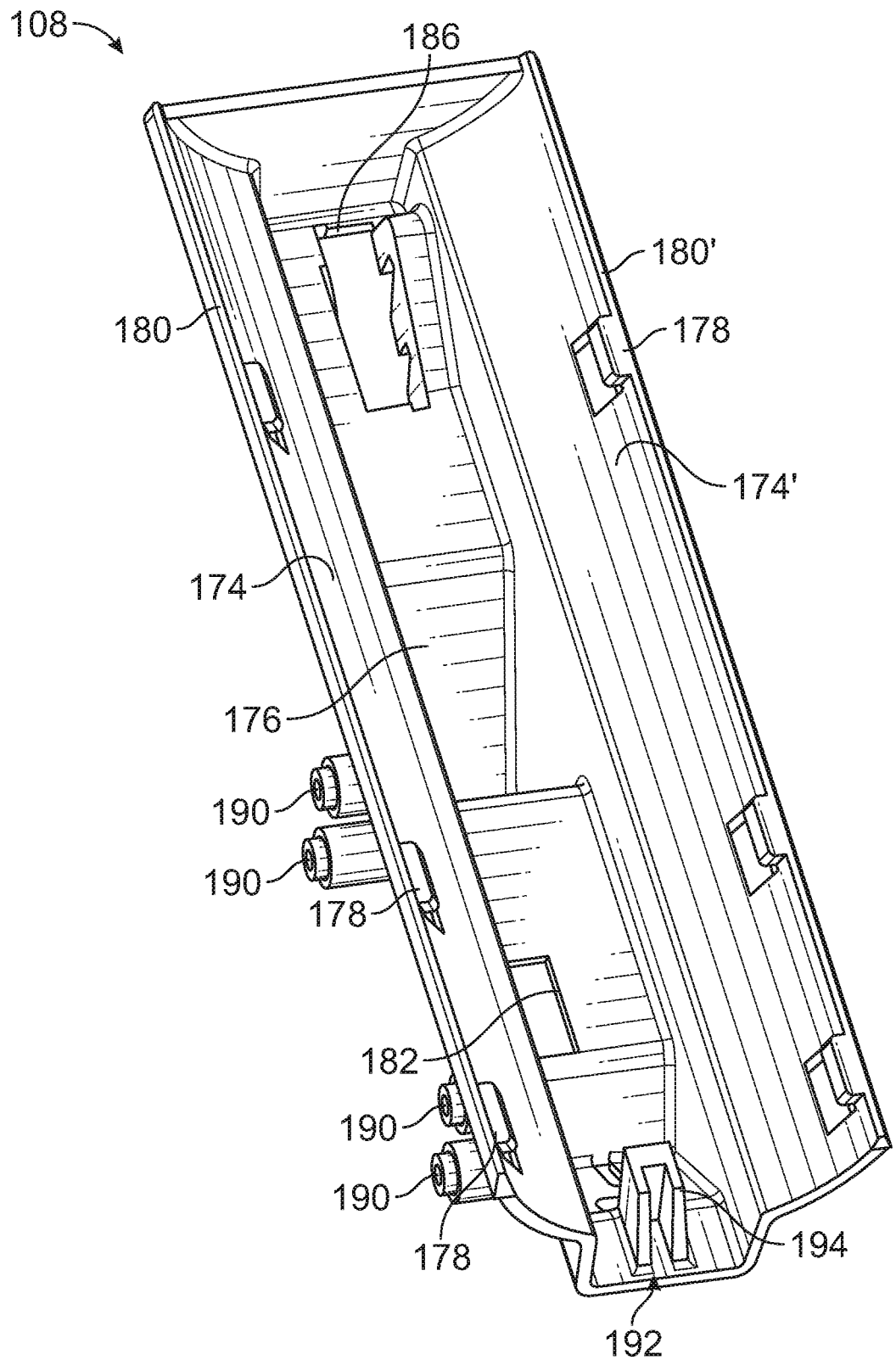
FIG. 9 is a perspective view of the chassis element with the tray removed showing a track portion, a sensor aperture, a gear aperture, a plurality of clip members and a stop member.

The chassis element 108 as shown in FIG. 9 includes curved track portions 174, 174' corresponding with the curved sidewall portions 158, 158' of the tray 106 and having a cavity 176 positioned therebetween. The chassis element 108 may also include a plurality of clips 178 extending from opposite edges 180, 180' of the curved track portions 174, 174' respectively to secure the tray 106 in slidable engagement therewith. An aperture 182 positioned in the cavity 176 of the chassis element 108 is included to permit a gear 184 of the motor 110 (FIG. 11) to directly engage the tray 106 to slidably move the tray 106 along the track portions 174, 174' of the chassis element 108. Another aperture 186 in the cavity 176 is aligned with a corresponding aperture 188 in the tray 106 to permit a pressure sensor (not shown) to extend through the chassis element 108 and tray 106 for detecting whether the canister housing 102 and canister 104 are engaged with the tray 106. Additionally, threaded apertures 190 of the chassis element 108 are used to couple the motor 110 to the chassis element 108 (as shown in FIG. 11) via, for example, threaded fasteners.

The chassis element 108 further includes a stop member 192 in the form of a protruding arm 194. The stop member 192 is positioned such that when the tray 106 is slidably advanced along the track portions 174, 174' of the chassis element 108, the channel 164 defined by the two elongate slots 160, 160' is advanced over the stop member 192 which will be described in more detail hereinafter with reference to operation of the spray canister device 100.

Figure 10:
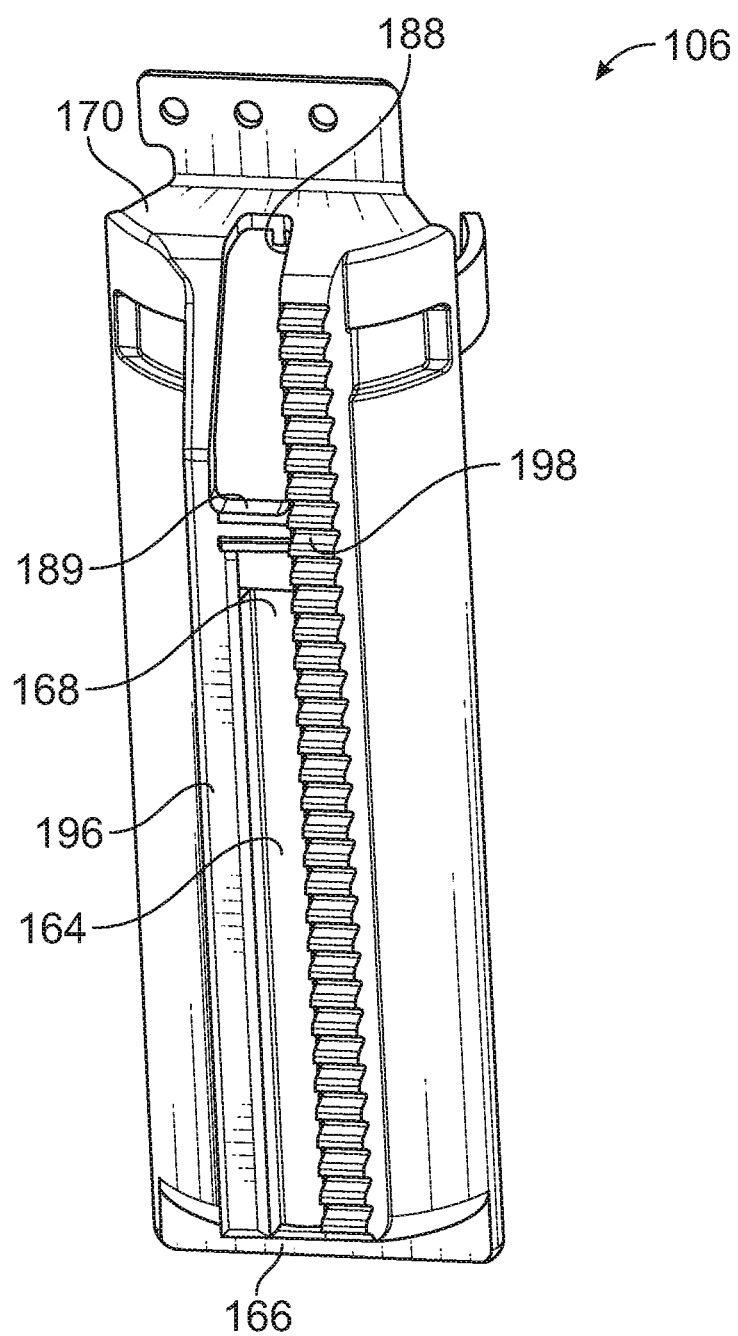
FIG. 10 is a perspective view of a distal side of the tray showing a toothed rack for engaging a pinion gear to slidably move the tray in the track portion of the chassis element.
Figure 11:
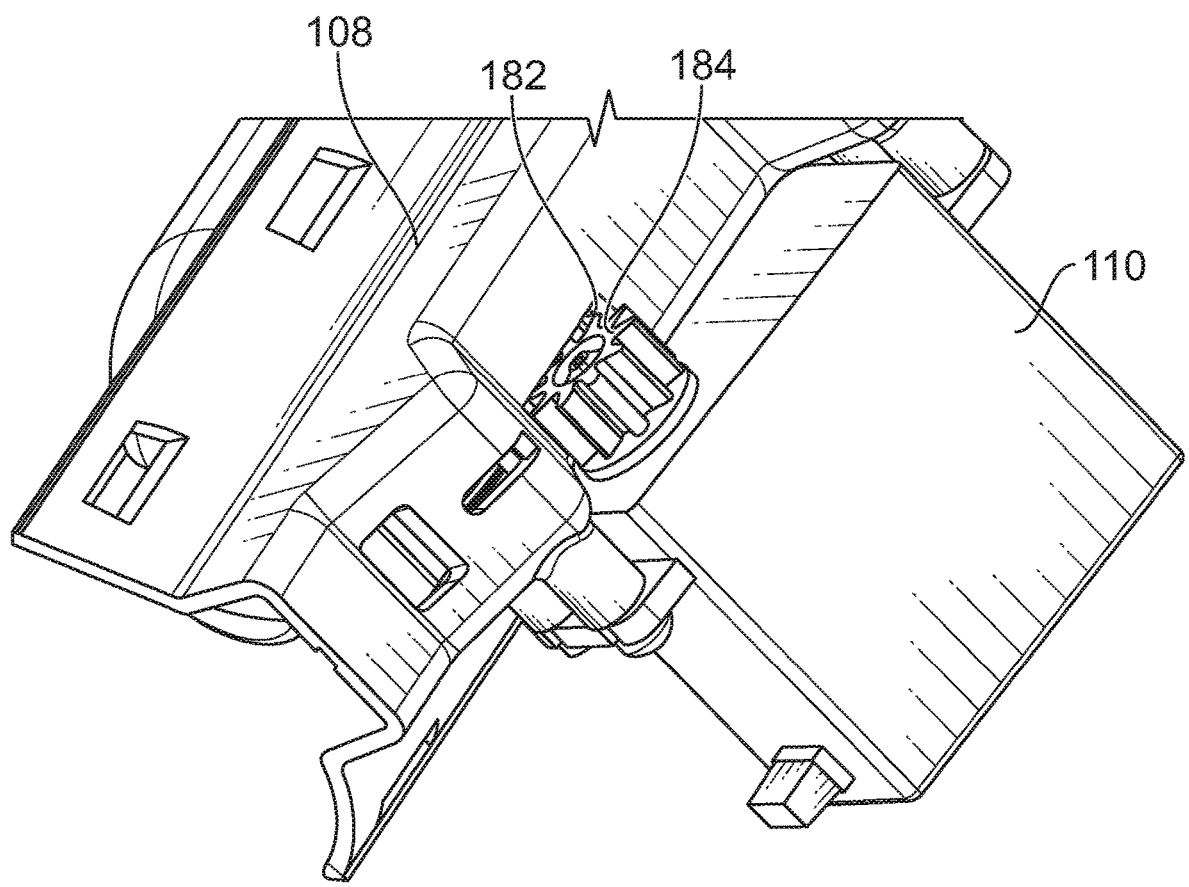
FIG. 11 is a perspective view of a portion of the bottom of the spray canister device showing the pinion gear rotatably coupled to the motor, and the engagement between the pinion gear and the toothed rack of the tray through the gear aperture of the chassis element.

FIG. 10 shows a rear perspective view of a distal side 196 of the tray 106 showing a toothed rack 198 which may be engaged by the pinion gear 184 connected to the motor 110 as shown in more detail in FIG. 11. Additionally, the aperture 188 of the tray 106 aligned with the aperture 186 of the chassis element 108 to accommodate the pressure sensor is sized such that the aperture 188 extends into a top surface 200 of the tray 106 to permit the tray 106 to advance along the track portions 174, 174' without interfering with the pressure sensor. The aperture 188 may further include a cross-bar 189 extending transverse the edges of the aperture 188 to inhibit the tray 106 from sliding beyond a predetermined point on the track portions 174, 174'. In operation, when the tray 106 is advanced to the extended position, the channel 164 of the tray is advanced over the stop member 192 until the cross-bar 189 abuts the stop member 192 thus inhibiting the tray 106 from overextending.

With respect to FIG. 11, showing a view from underneath the spray canister device 100, the motor 110 is rotatably coupled to the pinion gear 184 and is configured to rotate the pinion gear 184 positioned in the aperture 182 of the chassis element 108 with sufficient clearance such that the pinion gear 184 contacts the toothed rack 198 of the tray 106 to slidably move the tray 106 between the retracted position and the extended position. The motor 110 may be powered by a power source, such as a battery or connection to a wall outlet, and may cause the pinion gear 184 to slidably move the tray 106 between the retracted position and the extended position in response to a user input. For example, the spray canister device 100 may be controlled via, for example, a switch or a remote control using either a wired or wireless connection.

Figure 12:
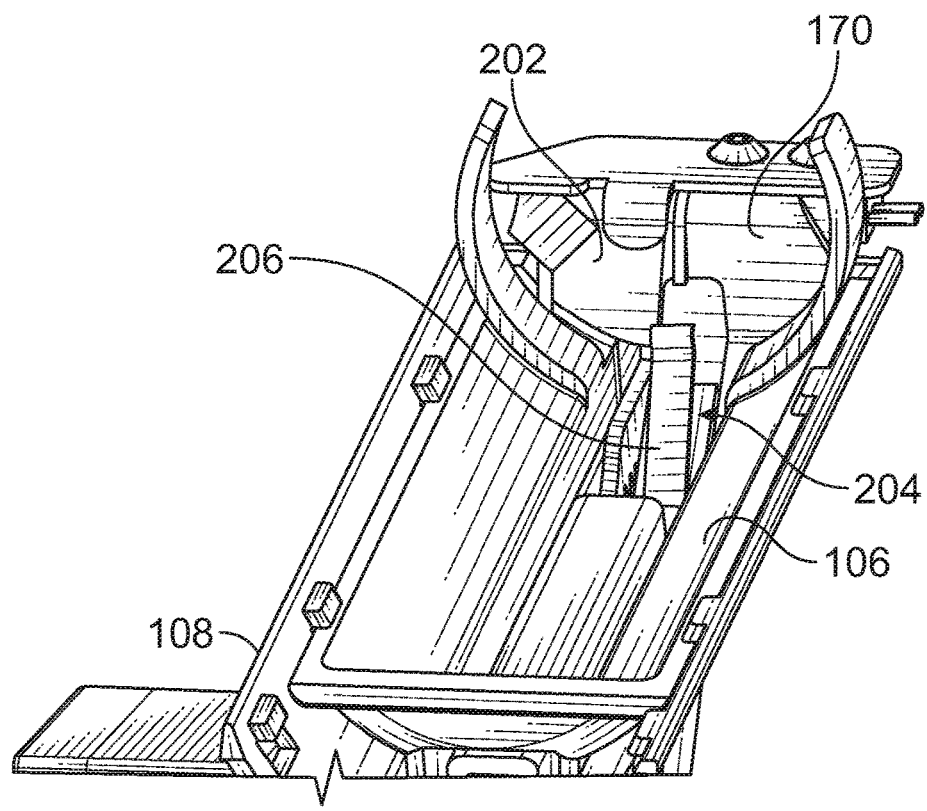
FIG. 12 is a perspective view of the tray slidably coupled to the chassis element showing a force sensor for detecting applied force and a pressure sensor for detecting whether the canister housing and canister are engaged with the tray.

As shown in FIG. 12, the spray canister device 100 may additionally include one or more sensors for detecting various operating characteristics of the spray canister device 100. For example, in the illustrated embodiment a force sensor 202 may be positioned proximate the compression member 170 of the tray 106 to detect a force that the compression member 170 is applying to the bottom surface 137 of the canister 104 to spray the liquid product. When the tray 106 is extended and the compression member 170 compresses the bottom surface 137 of the canister 104, the force sensor 202 may ensure that only a predetermined amount of force is applied to the bottom surface 137 such that the amount of liquid product sprayed may be controlled. For example, it may be desired that every operation of the spray canister device 100 sprays a substantially similar amount of the liquid product. A threshold force may be set for the force sensor 202 such that once a certain force is applied to the bottom surface 137 of the canister 104 by the compression member 170, the motor 110 reverses rotation, the force applied by the compression member 170 ceases, and the tray 106 is retracted back to the retracted position.

Additionally, a pressure sensor 204 as discussed above may be included for detecting the presence of the canister housing 102 and the canister 104 in the tray 106. As described, the pressure sensor 204 may be positioned proximate aperture 186 in the chassis element 108 and aperture 188 in the tray 106 and includes a depressible arm 206 that may be depressed when the canister 104 is secured by the rib member 172, 172' and the canister 104 and canister housing 102 are engaged with the tray 106. In some embodiments, when the depressible arm 206 of the pressure sensor 204 does not detect the presence of the canister 104 and the canister housing 102, movement of the tray 106 between the retracted position and the extended position may be inhibited, for example, via control circuitry of the spray canister device 100.

Figure 13:
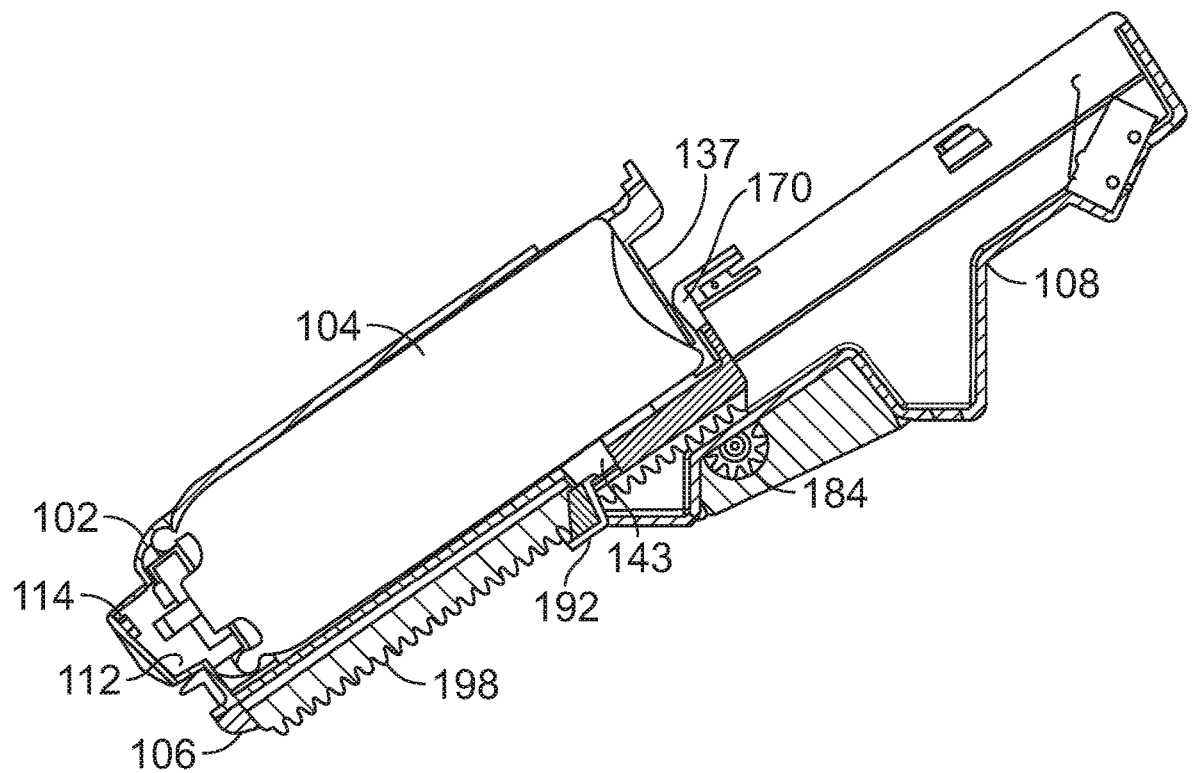
FIG. 13 is a cross-sectional view of the spray canister device of FIG. 1 showing the spray canister device in an extended position with the pinion gear engaging the toothed rack of the tray and the stop member of the chassis element abutting the locking structure of the canister housing.

Referring now to FIG. 13, a cross-sectional view of the spray canister device 100 in the extended position is shown. During initial operation, the tray 106, the canister housing 102, and the canister 104 are all advanced, together, towards the extended position of the spray canister device 100. As the tray 106, canister housing 102, and canister 104 are advanced outwards, the channel 164 formed between the elongate slots 160, 160' of the tray 106 (and shown more clearly in FIG. 10) travels over the stop member 192 of the chassis element 108. At a predetermined point corresponding with a desired length of extension, the second opening 168 of the channel 164 is advanced over the stop member 192 and the stop member 192 engages and abuts the locking structure 143 of the canister housing 102 and prevents the canister housing 102 and canister 104 from advancing along with the tray 106. So configured, the canister housing 102 and canister 104 are held static by the stop member 192 of the chassis element 108 and the tray 106 continues to advance towards the extended position. As this occurs, the compression member 170 of the tray 106 contacts and exerts force on the bottom surface 137 of the canister 104 to compress the actuator cap 112 against the interior surface 148 of the cap-shaped portion 124 of the canister housing 102 to spray the liquid product from the opening 120. So configured, the liquid product contained in the canister 104 is not sprayed until the tray 106 is in the extended position. After the liquid product has been sprayed, the reverse of the above-described process may occur. The motor 110 may reverse the direction of the pinion gear 184 to slidably moved the tray 106 back to the retracted position, thus disengaging the stop member 192 from the locking structure 143 of the canister housing 102 and returning the spray canister device 100 to the initial, retracted position.

Figure 14A:
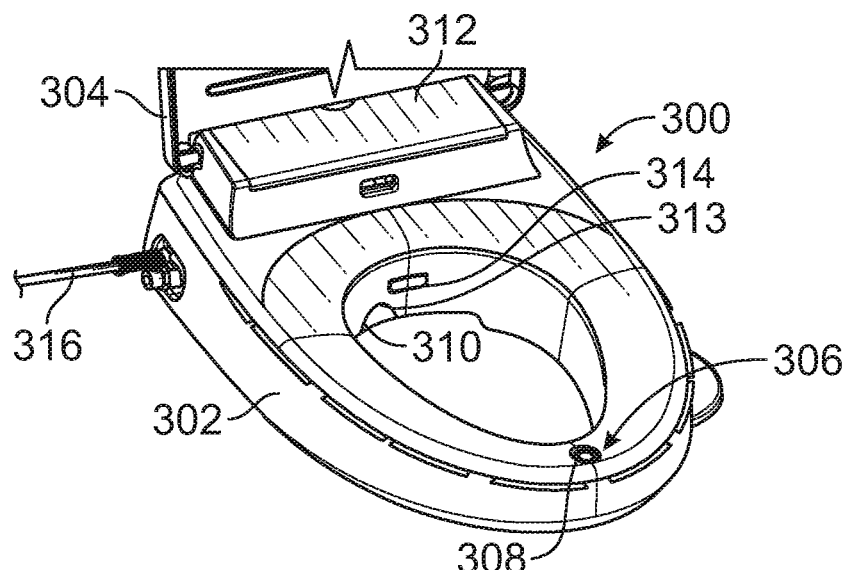
FIG. 14A is a perspective view of a portion of a toilet seat assembly including a base unit, a seat cover, a maintenance cover, and a spray canister device cover.

As described above, the spray canister device 100 may be positioned in a toilet seat assembly 300 including a base unit 302 and a seat cover 304. In addition to the spray canister device 100, the base unit 302 of the toilet seat assembly 300 may include various known features such as a spray nozzle common in bidet-type seats, a dryer to dry the perineal region, among others. Installation and operation of the spray canister device 100 in a toilet seat assembly 300 will be described with respect to FIGS. 14A through 14H. Referring to FIG. 14A, in order to control operation of the spray canister device 100, the toilet seat assembly may be operatively coupled to a user interface 306, such as a remote control, button, or switch, among others, for selectively spraying the liquid product contained in the spray canister device 100 on the perineal region of a user. For example, in the illustrated embodiment (seen in FIGS. 14A through 14H), the user interface 306 is in the form of a single button 308 on the front of the base unit 302. Actuation of the button 308 may cause the motor 110 to advance the tray 106 engaged with the canister housing 102 and canister 104 to the extended position to spray the liquid product on a perineal surface. Multiple actuations of the button 308 may be configured to cause varying amounts of the liquid product to be sprayed (i.e., one press may spray a first amount of the liquid product, two presses may spray a second amount of the liquid product greater than the first amount, etc.). In other embodiments, either wired or wireless remote controls may be used to operate the spray canister device 100.

As shown, the base unit 302 includes a spray canister device cover 310 and a maintenance cover 312, both in a closed position. The spray canister device cover 310 covers an opening 313 from which the tray 106, canister housing 102, and canister 104 may be advanced therethrough. In some embodiments, the spray canister device cover 310 may be held in the closed position via tension applied from a spring in the base unit 302. For example, the spring may be attached at one end to the spray canister device cover 310 and at another end to a portion of the base unit 302 such that advancing the tray 106, canister housing 102, and canister 104 through the opening 313 covered by the spray canister device cover 310 displaces the spray canister device cover 310 to permit the spray canister device 100 to perform a spraying operation. Once the tray 106, canister housing 102, and canister 104 are retracted back into the base unit 302, the spray canister device cover 310 may rebound to cover the opening via the tension applied by the spring. The maintenance cover 312 may be connected to the base unit 302 via a hinge such that it may be pivoted open to provide access to the components underneath.

Figure 14B:
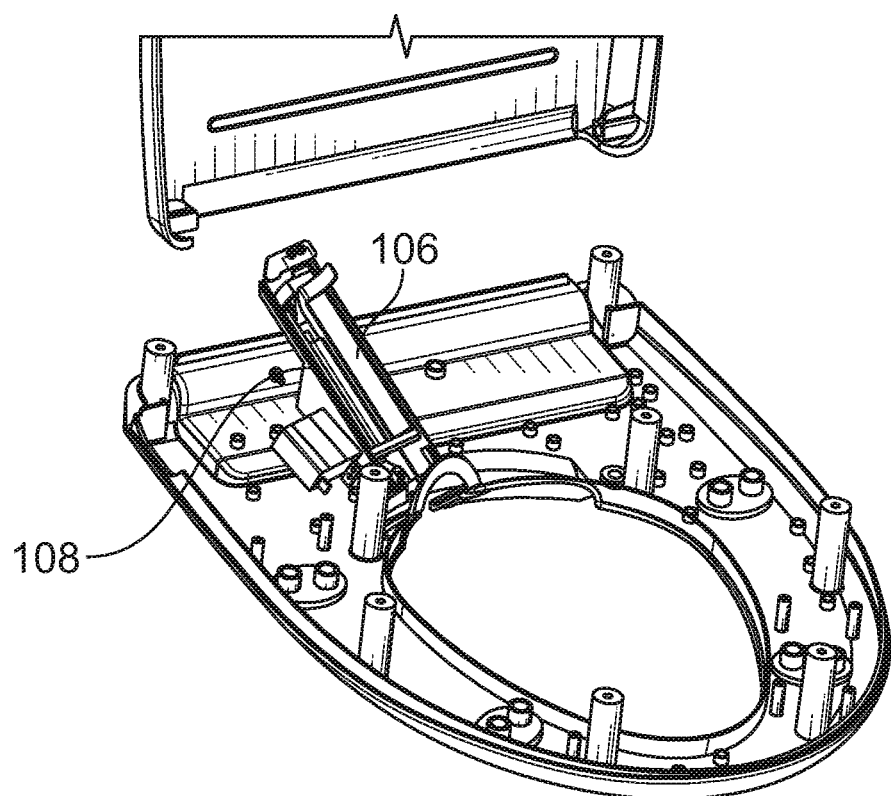
FIG. 14B is a perspective view of the toilet seat assembly of FIG. 14A with a portion removed to show the motor, the chassis element, and the tray slidably coupled thereto positioned in the base unit of the toilet seat assembly.

In the illustrated embodiment, the base unit 302 further includes a drying cover 314 covering a dryer which may be positioned in the base unit 302. The base unit 310 may be coupled to a power source such as a standard wall outlet via wire 316 to provide power to the motor 110 of the spray canister device 100 in addition to various other components contained in the base unit 310, such as the dryer or a spray nozzle if included. Both the chassis element 108, the tray 106, and the motor 110 of the spray canister device 100 are positioned inside of the base unit 310. As shown in FIG. 14B, the canister housing 102 and the canister 104 have not yet been engaged with the tray 106.

Figure 14C:
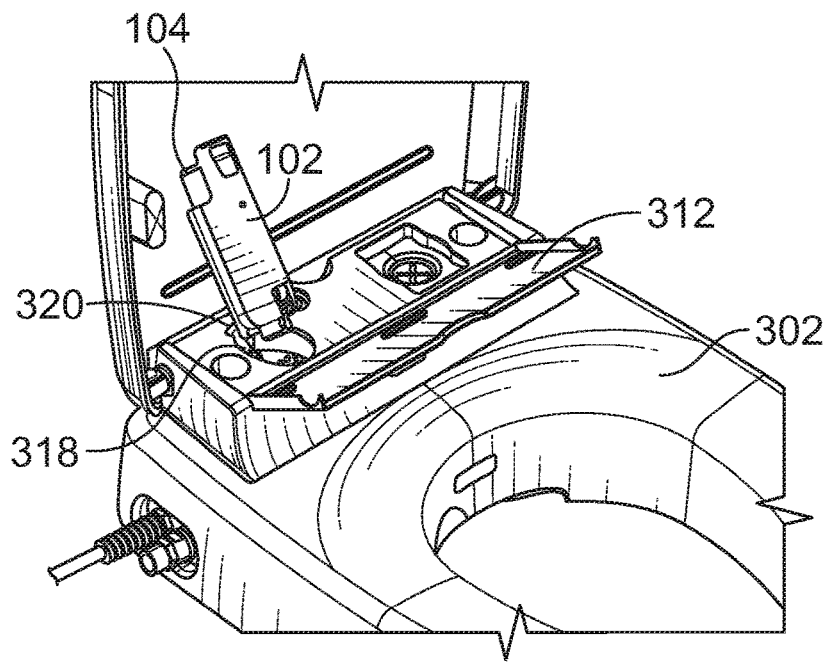
FIG. 14C is a perspective view of the toilet seat assembly of FIG. 14A showing the maintenance cover in an open position and the canister housing and canister being inserted in an aperture of the base unit for engagement with the tray slidably coupled to the chassis element.

In order to install the canister housing 102 and canister 104, a user may pivot open the maintenance cover 312 as shown in FIG. 14C. An aperture 318 covered by the maintenance cover 312 permits access to an interior of the base unit 302 for insertion and removal of the canister housing 102 and canister 104 in the toilet seat assembly 300. By one approach, the aperture 318 is shaped to facilitate insertion of the canister housing 102 and canister 104 in the base unit 302 for engagement with the tray 106 positioned therein. For example, the aperture 318 may be shaped to correspond with the shape of the canister housing 102 including the protruding member 138 shown in FIG. 6A to only permit the canister housing 102 and canister 104 to be inserted in the base unit 302 in a desired orientation, and may include a notch portion 320 to facilitate the insertion of the protruding member 138 in the form of elongate rails 140, 140'. So configured, the aperture 318 is shaped to receive the annular sleeve portion 116 of the canister housing 102 and the notch portion 320 is shaped to receive the protruding member 138, providing another keyed connection to facilitate insertion of the canister 104 and canister housing 102 in the desired orientation.

Once the liquid product within the canister is low or depleted, the canister housing 102 and canister 104 may be disengaged from the tray 106, removed through the aperture 318, and another canister housing 102 and canister 104 may be installed. As described above with respect to FIG. 2, the canister housing 102 may include the handle portion 123 for facilitating insertion and removal of the canister housing 102 and canister 104. The handle portion 123 provides a grip for the user to, for example, insert a finger therethrough to pull the canister housing 102 and canister 104 out of engagement with the tray 106 through the aperture 318 for removal. Generally, both the canister housing 102 and the canister 104 are disposable such that they may be disposed of once removed from the base unit 302 of the toilet seat assembly 300.

Figure 14D:
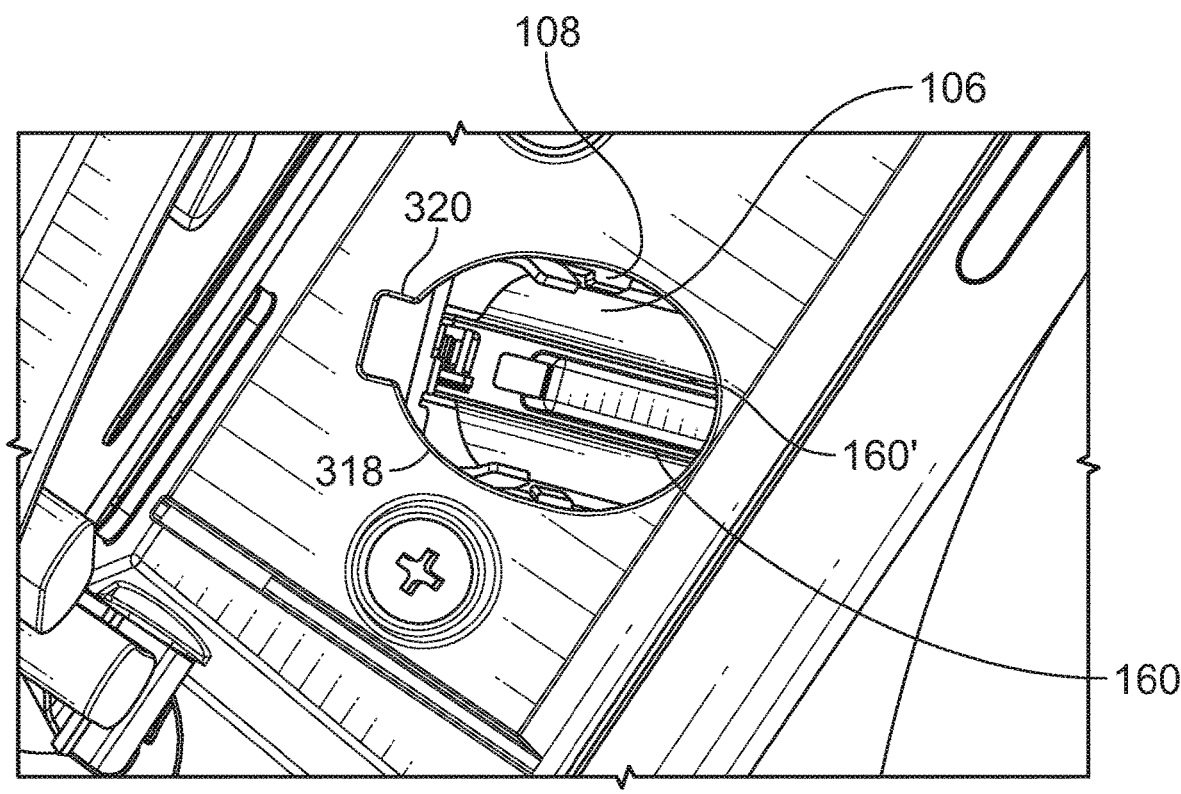
FIG. 14D is a top plan view of the aperture of the toilet seat assembly of FIG. 14A showing the tray including the elongate slots slidably coupled to the chassis element in the base unit.
Figure 14E:
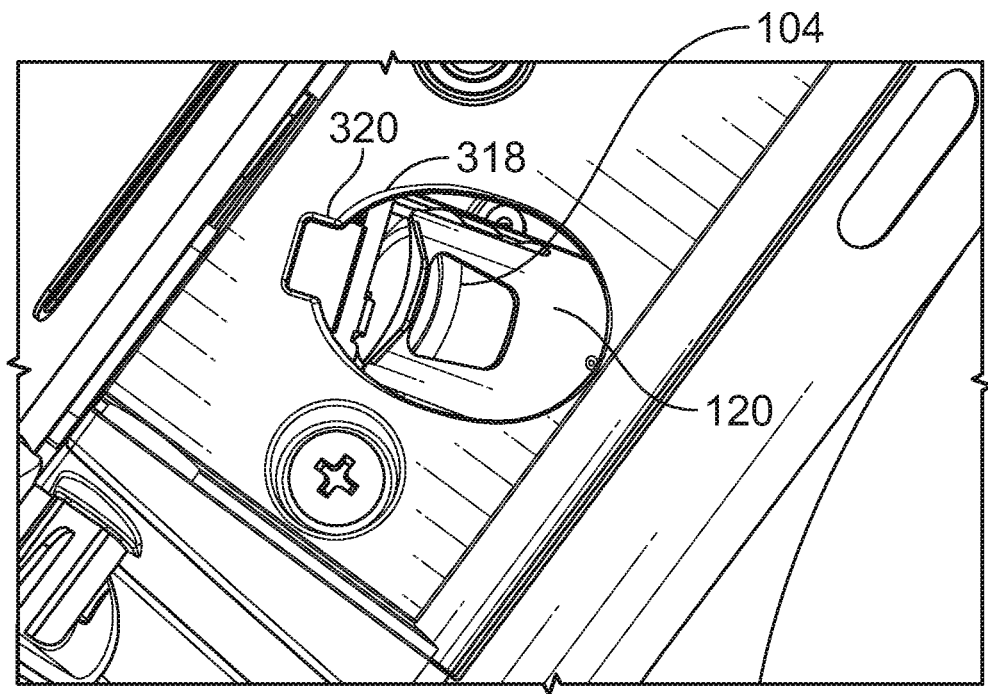
FIG. 14E is a view similar to FIG. 14D, showing the canister housing and canister engaged with the tray in the base unit of the toilet seat assembly.

FIG. 14D shows the aperture 318 from above before the canister housing 102 and canister 104 are installed in the toilet seat assembly 300 and engaged with the tray 106. The notch portion 320 is shown, and the aperture 318 is illustrated configured in an ovular shape to permit the canister housing 102 and canister 104 to be inserted at an angle. FIG. 14E shows the same view as FIG. 14D, but the canister housing 102 and canister 104 have now been installed through the aperture 318.

Figure 14F:
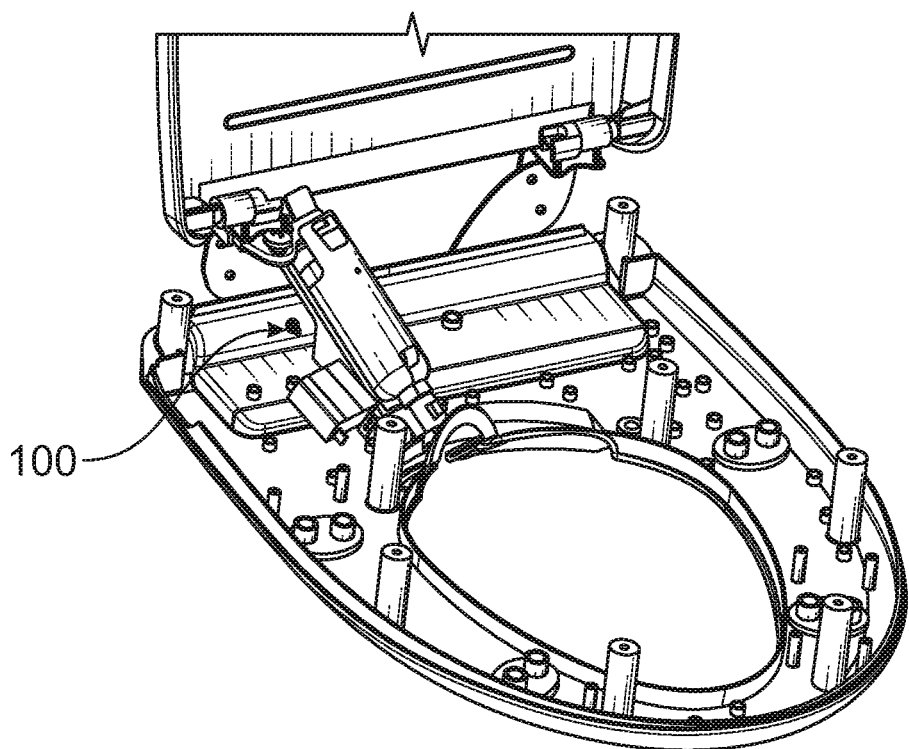
FIG. 14F is a view similar to FIG. 14B showing the canister housing and canister engaged with the tray in the base unit of the toilet seat assembly.

Referring to FIG. 14F, a portion of the base unit 302 of the toilet seat assembly 300 is in ghost to show the interior of the base unit 302 including the spray canister device 100. All other components contained within the base unit 302 are also in ghost to show the spray canister device 100 in the base unit 302 in the retracted position. From this position, the user may control operation of the spray canister device 100 via, for example, the button 308 or another remote-control device.

Figure 14G:
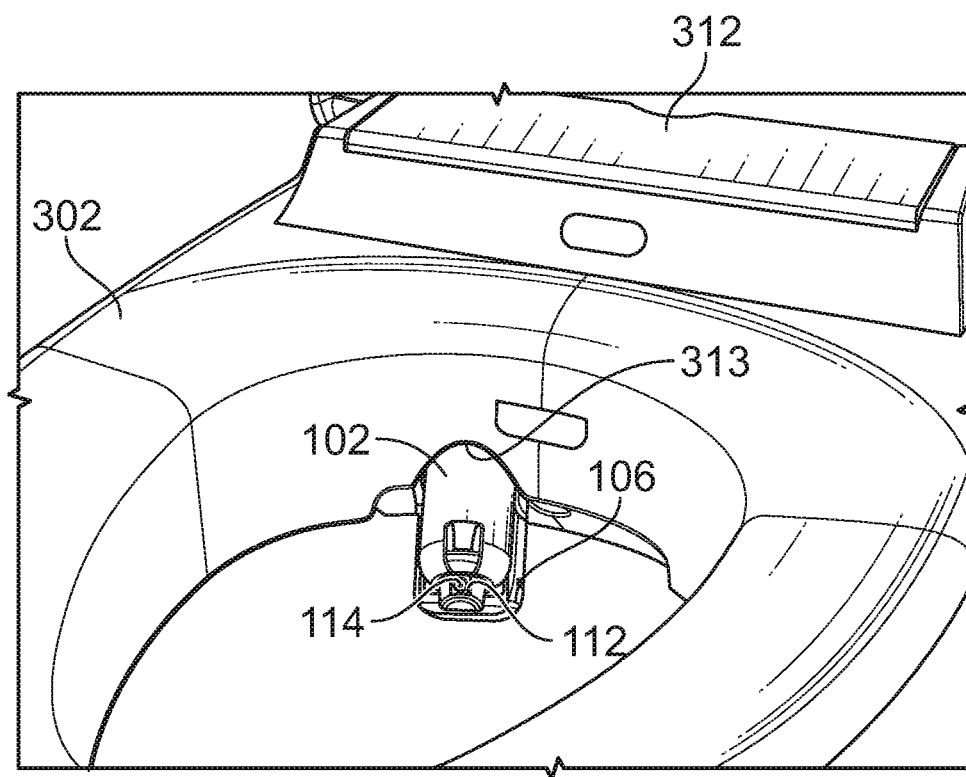
FIG. 14G is a perspective view of a portion of the base unit of the toilet seat assembly showing the tray, canister housing, and canister advancing through an opening of the base unit towards an extended position to spray a liquid product from the nozzle of the canister.
Figure 14H:
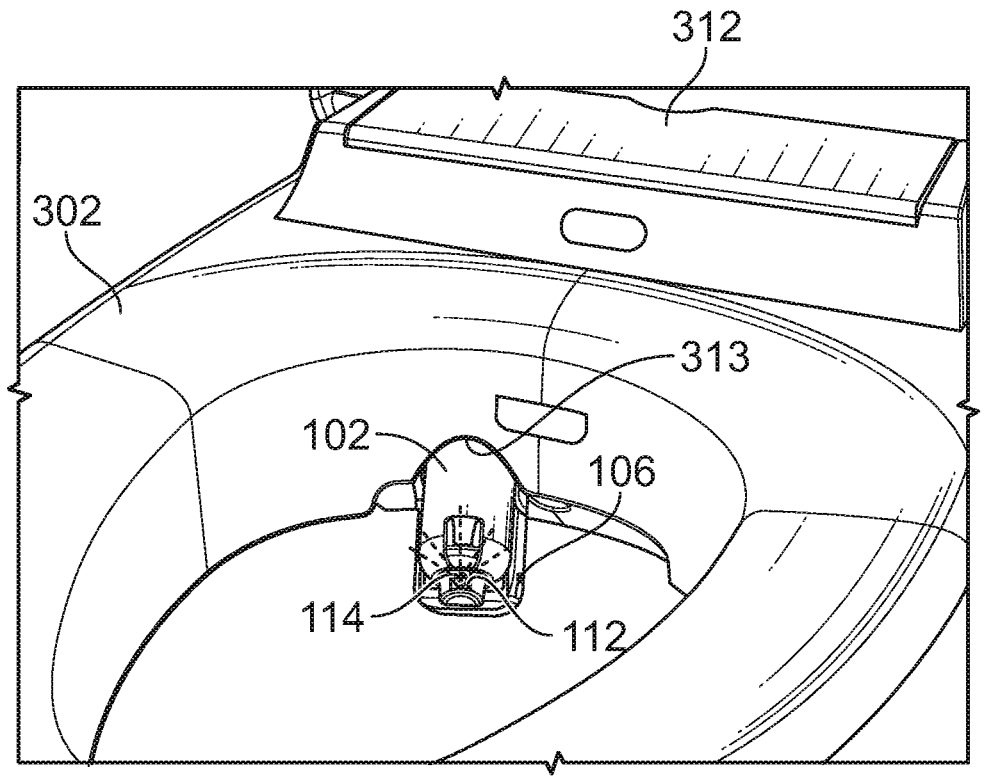
FIG. 14H is a perspective view similar to FIG. 14G showing the actuator cap of the canister being compressed against an interior surface of the cap-shaped portion to spray the liquid product contained therein.

In FIG. 14G, the spray canister device 100 is shown just short of the fully extended position with the tray 106, canister housing 102, and canister 104 advanced through the opening 313 of the base unit 302 ready to apply the liquid product to the perineal region of the user. At this point, the stop member 192 of the chassis element 108 is contacting the locking structure 143 of the canister housing 102 to inhibit the canister housing 102 and canister 104 from advancing any further out of the base unit 302. As the tray 106 continues to advance further, as shown in FIG. 14H, the compression member 170 of the tray 106 applies force to the bottom surface 137 of the canister 104 to compress the actuator cap 112 against the interior surface 148 of the cap-shaped portion 124 to release the liquid product and spray the liquid product through the nozzle 114.

Once the predetermined amount of liquid product has been sprayed onto the perineal region of the user, the tray 106, canister housing 102, and canister 104 may be retracted back into the base unit 302 via the motor 110 and the spray canister device cover 310 may rebound to cover the opening 313 via the spring such that once the spray canister device returns to the retracted position a single spraying operation has been completed.

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. The disclosure is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the disclosure and does not pose a limitation on the scope of the disclosure. Any statement herein as to the nature or benefits of the disclosed device or of the preferred embodiments is not intended to be limiting. This invention includes all modifications and equivalents of the subject matter recited herein as permitted by applicable law. Moreover, any combination of the above-described elements in all possible variations thereof is encompassed by the disclosure unless otherwise indicated herein or otherwise clearly contradicted by context. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A spray canister device for use in a toilet seat assembly, the spray canister device comprising:
   a canister housing comprising an annular sleeve portion, an end portion, at least one protruding member extending along the annular sleeve portion, and an opening extending at least partially along the end portion;
   a canister including an actuator cap, the canister storing a liquid product therein, the actuator cap including a spray nozzle;
   a chassis element; and
   a tray slidably coupled to the chassis element, the tray including at least one elongate slot for receiving one of the at least one protruding members of the canister housing to provide mating engagement between the canister housing and the tray; and
   wherein the canister is positioned in the annular sleeve portion of the canister housing, the actuator cap received at least partially in the end portion of the canister housing, the spray nozzle positioned proximate the opening of the canister housing; and
   wherein the canister housing and the canister are movable relative to one another to cause release of the liquid product from the spray nozzle of the actuator cap and through the opening of the canister housing.

2. The spray canister device of claim 1, further comprising a motor operatively connected to the tray, the motor configured to cause slidable movement of the tray between a retracted position and an extended position along a track portion of the chassis element.

3. The spray canister device of claim 1, wherein the canister housing further comprises a handle portion to facilitate at least one of engagement between the canister housing and the tray and disengagement between the canister housing and the tray.

4. The spray canister device of claim 1, wherein a first surface of the actuator cap includes a first mating portion, and wherein an interior surface of the end portion of the canister housing includes a second mating portion, the second mating portion of the interior surface configured to correspond with, and engage, the first mating portion of the actuator cap to facilitate alignment of the spray nozzle with the opening.

5. The spray canister device of claim 4, wherein the first surface of the actuator cap further includes a concave portion corresponding with a convex portion of the interior surface of the end portion.

6. The spray canister device of claim 1, wherein the tray further includes one or more rib elements for at least partially surrounding and engaging the canister to secure the canister housing and the canister to the tray.

7. The spray canister device of claim 1, wherein the liquid product comprises one or more of skin protectants, ointments, mineral oil, silicone fluids, dimethicone, cyclomethycone, petrolatum, cod liver oil, lanolin, zinc oxide, talc, calamine, kaolin, topical starch, allantoin, barrier materials, skin moisturizers, skin lotions, moisturizing creams, skin sealants, water, medicaments, cleaning solutions, moisture barriers, and combinations thereof.

8. The spray canister device of claim 1, wherein the at least one protruding member comprises two elongate rails, and wherein a locking structure extends between the two elongate rails for abutment with a stop member of the chassis element.

9. The spray canister device of claim 8, wherein abutment between the locking structure and the stop member inhibits movement of the canister housing to facilitate relative movement between the canister housing and the canister to compress the actuator cap thereof.

10. The spray canister device of claim 1, further comprising one or more sensors, the one or more sensors comprising one or more of a force sensor for detecting an amount of force applied to the canister, and a pressure sensor for detecting whether the canister housing is engaged with the tray.

11. The spray canister device of claim 2, wherein the tray includes a toothed rack, and wherein the motor is rotatably coupled to a toothed gear configured to engage with the toothed rack, the motor configured to rotate the toothed gear to slidably move the tray between the retracted position and the extended position.

12. The spray canister device of claim 1, wherein the canister housing includes a handle portion extending from the annular sleeve portion to facilitate engagement between the canister housing and the tray.

13. A spray canister housing for a canister containing a liquid product, the spray canister housing comprising:
an annular sleeve portion, an end portion, at least one protruding member extending along the annular sleeve portion, and an opening extending at least partially along the end portion;
wherein a canister including a rim surface is at least partially received in the annular sleeve portion; and
wherein the annular sleeve portion includes a finger portion extending at least partially in the opening, the finger portion configured to engage with and abut at least a portion of the rim surface upon insertion of the canister in the annular sleeve portion to inhibit removal thereof.

14. The spray canister housing of claim 13, wherein an interior surface of the end portion includes a first mating portion corresponding with and configured to engage a second mating portion of the canister to facilitate alignment of the canister in the canister housing.

15. The spray canister housing of claim 13 further comprising a handle portion extending from the annular sleeve portion.

16. A spray canister device for installation in a toilet seat assembly, the spray canister device comprising:
a canister housing with an annular sleeve portion and an end portion, the end portion including an opening;
a canister including an actuator cap; and
a chassis and slidable tray positioned in the toilet seat assembly, the chassis and the slidable tray configured to move the canister and canister housing;
wherein the spray canister device includes:
a first keyed connection formed by at least one protruding member of the canister housing extending along the annular sleeve portion and an aperture of the toilet seat assembly having a notch portion, the aperture shaped to receive the annular sleeve portion of the spray canister housing and the notch portion shaped to receive the protruding member of the spray canister housing to align the spray canister housing upon insertion in the aperture; and
a second keyed connection between the actuator cap of the canister and the end portion of the canister housing.

17. The spray canister device of claim 16, wherein the annular sleeve portion is configured to receive the canister at least partially therein, wherein the canister is configured to contain a liquid product.

18. The spray canister device of claim 17, wherein the end portion of the canister housing includes a first mating surface corresponding with and configured to engage a second mating surface of the actuator cap, the first and second mating surfaces comprising the second keyed connection.

19. The spray canister device of claim 18, wherein the engagement between the first and second mating surfaces is configured to facilitate alignment between a nozzle of the actuator cap and the opening of the canister housing.

20. The spray canister device of claim 16, further including a third keyed connection between the at least one protruding member of the canister housing and the slidable tray, wherein the at least one protruding member is configured to engage with the slidable tray to facilitate alignment of the canister housing therewith.

* * * * *